(12) United States Patent
Weng et al.

(10) Patent No.: US 12,163,184 B2
(45) Date of Patent: Dec. 10, 2024

(54) METHODS AND COMPOSITIONS FOR FORMING LIGATION PRODUCTS

(71) Applicant: ACCURAGEN HOLDINGS LIMITED, Grand Cayman (KY)

(72) Inventors: Li Weng, Fremont, CA (US);
Shengrong Lin, Fremont, CA (US);
Malek Faham, Burlingame, CA (US)

(73) Assignee: ACCURAGEN HOLDINGS LIMITED, George Town (KY)

( * ) Notice: Subject to any disclaimer, the term of this patent is extended or adjusted under 35 U.S.C. 154(b) by 1184 days.

(21) Appl. No.: 15/780,370

(22) PCT Filed: Dec. 2, 2016

(86) PCT No.: PCT/US2016/064853
§ 371 (c)(1),
(2) Date: Nov. 8, 2018

(87) PCT Pub. No.: WO2017/096322
PCT Pub. Date: Jun. 8, 2017

(65) Prior Publication Data
US 2018/0363039 A1    Dec. 20, 2018

Related U.S. Application Data

(60) Provisional application No. 62/262,883, filed on Dec. 3, 2015.

(51) Int. Cl.
*C12P 19/34* (2006.01)
*C12M 1/34* (2006.01)
(Continued)

(52) U.S. Cl.
CPC ............. *C12Q 1/6839* (2013.01); *C12M 1/34* (2013.01); *C12Q 1/68* (2013.01); *C12Q 1/6806* (2013.01); *C12Q 1/6855* (2013.01)

(58) Field of Classification Search
USPC ..... 435/6.1, 6.11, 91.1, 91.2, 91.51; 436/94, 436/501; 536/23.1, 24.3, 24.33, 25.3
See application file for complete search history.

(56) References Cited

U.S. PATENT DOCUMENTS 5,130,238 A    7/1992  Malek et al.
5,234,809 A    8/1993  Boom et al.
(Continued)

FOREIGN PATENT DOCUMENTS

AU         9057901 A        3/2002
CN       101432439 A        5/2009
(Continued)

OTHER PUBLICATIONS

Konry et al. Microsphere-Based Rolling Circle Amplification Microarray for the Detection of DNA and Proteins in a Single. AssayAnal. Chem. 2009; 81: 5777-5782. (Year: 2009).*

(Continued)

*Primary Examiner* — Frank W Lu
(74) *Attorney, Agent, or Firm* — WILSON SONSINI GOODRICH & ROSATI

(57) ABSTRACT

In some aspects, the present disclosure provides methods for forming ligation products comprising single-stranded polynucleotides. Ligation products formed by various aspects of the present disclosure can be useful for various applications, including but not limited to sequence analysis. In some embodiments, the ligation products comprise cell-free polynucleotides. In some aspects, the present disclosure provides reaction mixtures, kits and complexes consistent with the methods herein.

10 Claims, 10 Drawing Sheets

(51) Int. Cl.
  *C12Q 1/68* (2018.01)
  *C12Q 1/6806* (2018.01)
  *C12Q 1/6839* (2018.01)
  *C12Q 1/6855* (2018.01)

(56) References Cited

U.S. PATENT DOCUMENTS

| | | |
|---|---|---|
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |
| 5,492,808 A | 2/1996 | De et al. |
| 5,494,810 A | 2/1996 | Barany et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | De et al. |
| 5,648,212 A | 7/1997 | Albertsen et al. |
| 5,648,245 A | 7/1997 | Fire et al. |
| 5,691,454 A | 11/1997 | Albertsen et al. |
| 5,693,470 A | 12/1997 | De et al. |
| 5,693,536 A | 12/1997 | Vogelstein et al. |
| 5,705,365 A | 1/1998 | Ryder et al. |
| 5,705,628 A | 1/1998 | Hawkins et al. |
| 5,710,029 A | 1/1998 | Ryder et al. |
| 5,783,666 A | 7/1998 | Albertsen et al. |
| 5,807,692 A | 9/1998 | Kinzler et al. |
| 5,830,676 A | 11/1998 | Vogelstein et al. |
| 5,830,711 A | 11/1998 | Barany et al. |
| 5,834,252 A * | 11/1998 | Stemmer ............... C12N 15/10 |
| | | 435/195 |
| 5,837,443 A | 11/1998 | De et al. |
| 5,854,033 A | 12/1998 | Lizardi |
| 5,871,925 A | 2/1999 | De et al. |
| 5,871,968 A | 2/1999 | Kinzler et al. |
| 5,888,779 A | 3/1999 | Kacian et al. |
| 5,939,291 A | 8/1999 | Loewy et al. |
| 5,942,391 A | 8/1999 | Zhang et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,143,495 A * | 11/2000 | Lizardi ............... C12Q 1/6862 |
| | | 435/6.12 |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,569,647 B1 | 5/2003 | Zhang et al. |
| 6,582,908 B2 | 6/2003 | Fodor et al. |
| 6,593,086 B2 | 7/2003 | Zhang |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,815,167 B2 | 11/2004 | Crothers et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield et al. |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | De et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,424,368 B2 | 9/2008 | Huang et al. |
| 7,537,897 B2 | 5/2009 | Brenner et al. |
| 7,553,619 B2 | 6/2009 | Kumar et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski et al. |
| 8,048,629 B2 | 11/2011 | Gocke et al. |
| 8,209,130 B1 | 6/2012 | Kennedy et al. |
| 8,361,726 B2 | 1/2013 | Gocke et al. |
| 8,563,477 B2 | 10/2013 | Smith et al. |
| RE44,596 E | 11/2013 | Stroun et al. |
| 8,835,358 B2 | 9/2014 | Fodor et al. |
| 9,217,167 B2 | 12/2015 | Heller et al. |
| 9,260,753 B2 | 2/2016 | Xie et al. |
| 10,155,980 B2 | 12/2018 | Weng et al. |
| 10,443,087 B2 | 10/2019 | Rigatti et al. |
| 10,752,942 B2 * | 8/2020 | Weng ................... C12Q 1/6858 |
| 11,578,359 B2 | 2/2023 | Weng et al. |
| 11,597,973 B2 | 3/2023 | Tang |
| 2002/0042061 A1 | 4/2002 | Yang et al. |
| 2002/0168645 A1 | 11/2002 | Taylor |
| 2003/0032024 A1 | 2/2003 | Lizardi |
| 2003/0100077 A1 | 5/2003 | Korte et al. |
| 2003/0207295 A1 * | 11/2003 | Gunderson .......... C12Q 1/6874 |
| | | 435/6.12 |
| 2004/0058378 A1 | 3/2004 | Kong et al. |
| 2004/0067511 A1 | 4/2004 | Thomas |
| 2006/0029953 A1 | 2/2006 | Sharf |
| 2006/0228721 A1 | 10/2006 | Leamon et al. |
| 2007/0020646 A1 | 1/2007 | Hoon et al. |
| 2007/0087362 A1 | 4/2007 | Church et al. |
| 2007/0099208 A1 * | 5/2007 | Drmanac ............... C07K 1/047 |
| | | 435/6.12 |
| 2007/0134128 A1 | 6/2007 | Korlach |
| 2008/0021205 A1 | 1/2008 | Blau et al. |
| 2008/0039417 A1 | 2/2008 | Wang et al. |
| 2008/0160511 A1 | 7/2008 | Dawson et al. |
| 2008/0199916 A1 * | 8/2008 | Zheng .................. C12Q 1/6844 |
| | | 435/91.2 |
| 2009/0099041 A1 | 4/2009 | Church et al. |
| 2009/0136924 A1 | 5/2009 | Larionov et al. |
| 2010/0028873 A1 * | 2/2010 | Belouchi ............... C12Q 1/6855 |
| | | 435/6.12 |
| 2010/0075384 A1 | 3/2010 | Kong et al. |
| 2010/0115744 A1 | 5/2010 | Fong |
| 2010/0291548 A1 * | 11/2010 | Sharaf ................. C12Q 1/6823 |
| | | 435/6.11 |
| 2010/0304989 A1 | 12/2010 | Von et al. |
| 2011/0003705 A1 | 1/2011 | Lowe et al. |

(56) References Cited

U.S. PATENT DOCUMENTS

| | | | |
|---|---|---|---|
| 2011/0124052 A1* | 5/2011 | Zheng | C12Q 1/6844 435/91.2 |
| 2011/0151438 A9 | 6/2011 | Nautiyal et al. | |
| 2011/0237444 A1 | 9/2011 | Clancy et al. | |
| 2011/0288284 A1 | 11/2011 | Makarov | |
| 2011/0319299 A1 | 12/2011 | Osborne et al. | |
| 2012/0115744 A1 | 5/2012 | Raymond et al. | |
| 2012/0157326 A1 | 6/2012 | Tisi et al. | |
| 2012/0164651 A1 | 6/2012 | Kazakov et al. | |
| 2013/0116130 A1 | 5/2013 | Fu et al. | |
| 2013/0178369 A1* | 7/2013 | Burns | G01N 1/30 506/9 |
| 2013/0217023 A1 | 8/2013 | Godwin et al. | |
| 2013/0224740 A1 | 8/2013 | Thierry et al. | |
| 2013/0244885 A1 | 9/2013 | Wang et al. | |
| 2013/0331288 A1 | 12/2013 | Gunderson et al. | |
| 2014/0051154 A1 | 2/2014 | Hyland et al. | |
| 2014/0066317 A1 | 3/2014 | Talasaz et al. | |
| 2014/0121116 A1 | 5/2014 | Richards et al. | |
| 2014/0154683 A1 | 6/2014 | Vogelstein et al. | |
| 2014/0221329 A1 | 8/2014 | Cronin et al. | |
| 2014/0227705 A1 | 8/2014 | Vogelstein et al. | |
| 2014/0234850 A1 | 8/2014 | Zhang et al. | |
| 2014/0274740 A1 | 9/2014 | Srinivasan et al. | |
| 2014/0295498 A1 | 10/2014 | Turner et al. | |
| 2014/0296081 A1 | 10/2014 | Diehn et al. | |
| 2014/0336236 A1 | 11/2014 | Cronin et al. | |
| 2015/0031035 A1 | 1/2015 | Kvam et al. | |
| 2015/0033372 A1 | 1/2015 | Bradley et al. | |
| 2015/0044687 A1 | 2/2015 | Schmitt et al. | |
| 2015/0111789 A1 | 4/2015 | Betts et al. | |
| 2015/0126376 A1 | 5/2015 | Bielas et al. | |
| 2015/0133391 A1 | 5/2015 | De Vlaminick et al. | |
| 2015/0141292 A1 | 5/2015 | Fodor et al. | |
| 2015/0147815 A1 | 5/2015 | Babiarz et al. | |
| 2015/0152482 A1* | 6/2015 | Zheng | C12Q 1/6844 506/26 |
| 2015/0315636 A1 | 11/2015 | Nadeau et al. | |
| 2015/0361492 A1 | 12/2015 | Vogelstein et al. | |
| 2015/0366866 A1 | 12/2015 | Ali et al. | |
| 2016/0040229 A1 | 2/2016 | Talasaz et al. | |
| 2016/0145691 A1 | 5/2016 | Cronin et al. | |
| 2016/0201135 A1 | 7/2016 | Cronin et al. | |
| 2016/0304954 A1 | 10/2016 | Lin et al. | |
| 2016/0319345 A1 | 11/2016 | Gnerre et al. | |
| 2017/0204456 A1 | 7/2017 | Nobile et al. | |
| 2017/0204459 A1* | 7/2017 | Barany | C12Q 1/6809 |
| 2017/0275609 A1 | 9/2017 | Geng et al. | |
| 2017/0362639 A1 | 12/2017 | Wilson | |
| 2018/0298434 A1 | 10/2018 | Weng et al. | |
| 2018/0363052 A1 | 12/2018 | Schmitt et al. | |
| 2019/0119743 A1 | 4/2019 | Weng et al. | |
| 2019/0241935 A1 | 8/2019 | Makarov et al. | |
| 2019/0323073 A1 | 10/2019 | Lin et al. | |
| 2020/0010883 A1 | 1/2020 | Weng et al. | |
| 2020/0010884 A1 | 1/2020 | Faham et al. | |
| 2020/0080141 A1 | 3/2020 | Weng et al. | |
| 2023/0287485 A1 | 9/2023 | Weng et al. | |
| 2023/0357836 A1 | 11/2023 | Weng et al. | |

FOREIGN PATENT DOCUMENTS

| | | |
|---|---|---|
| CN | 101935697 A | 1/2011 |
| CN | 101985654 A | 3/2011 |
| CN | 102625850 A | 8/2012 |
| CN | 103717752 A | 4/2014 |
| CN | 104745679 A | 7/2015 |
| CN | 104946737 A | 9/2015 |
| EP | 0684315 A1 | 11/1995 |
| EP | 0518650 B1 | 1/1997 |
| EP | 0390323 B1 | 12/1998 |
| EP | 0929694 A1 | 7/1999 |
| EP | 0580596 B1 | 7/2000 |
| EP | 0569527 B1 | 3/2001 |
| EP | 0730648 B1 | 8/2004 |
| EP | 2396430 B1 | 5/2013 |
| EP | 2722401 A1 * | 4/2014 ........... C12Q 1/6806 |
| EP | 2828218 A1 | 1/2015 |
| EP | 3080298 B1 | 10/2018 |
| JP | 2002503948 A | 2/2002 |
| JP | 2002538840 A | 11/2002 |
| JP | 2004512134 A | 4/2004 |
| JP | 2006516410 A | 7/2006 |
| JP | 2008526228 A | 7/2008 |
| JP | 2009500004 A | 1/2009 |
| JP | 2011505161 A | 2/2011 |
| JP | 2013143966 A | 7/2013 |
| JP | 2014138597 A | 7/2014 |
| JP | 2016507246 A | 3/2016 |
| WO | WO-9844151 A1 | 10/1998 |
| WO | WO-0004192 A1 | 1/2000 |
| WO | WO-0049176 A1 | 8/2000 |
| WO | WO-0061741 A1 | 10/2000 |
| WO | WO-0118230 A1 | 3/2001 |
| WO | WO-0120035 A2 | 3/2001 |
| WO | WO-0138580 A2 | 5/2001 |
| WO | WO-2007024653 A2 | 3/2007 |
| WO | WO-2005026329 A3 | 8/2007 |
| WO | WO-2007133703 A2 | 11/2007 |
| WO | WO-2007140417 A2 | 12/2007 |
| WO | WO-2007140417 A3 | 2/2008 |
| WO | WO-2007024653 A3 | 4/2008 |
| WO | WO-2008070352 A3 | 10/2008 |
| WO | WO-2007117832 A3 | 12/2008 |
| WO | WO-2013074632 A1 | 5/2013 |
| WO | WO-2013142389 A1 | 9/2013 |
| WO | WO-2013181170 A1 | 12/2013 |
| WO | WO-2013181276 A1 | 12/2013 |
| WO | WO-2014014498 A1 | 1/2014 |
| WO | WO-2014015084 A2 | 1/2014 |
| WO | WO-2014070946 A1 | 5/2014 |
| WO | WO-2014145128 A2 | 9/2014 |
| WO | WO-2014176575 A1 | 10/2014 |
| WO | WO-2015079042 A1 | 6/2015 |
| WO | WO-2015089333 A1 * | 6/2015 ........... C12Q 1/6806 |
| WO | WO-2015100427 A1 | 7/2015 |
| WO | WO-2016053638 A1 | 4/2016 |
| WO | WO-2016187583 A1 * | 11/2016 ........... A41C 3/0064 |
| WO | WO-2017062863 A1 * | 4/2017 ............... C12Q 1/68 |
| WO | WO-2017096322 A1 | 6/2017 |
| WO | WO-2017201102 A1 | 11/2017 |
| WO | WO-2017223366 A1 | 12/2017 |
| WO | WO-2018035170 A1 | 2/2018 |
| WO | WO-2019241290 A1 | 12/2019 |
| WO | WO-2020049176 A1 | 3/2020 |

OTHER PUBLICATIONS

Zhao et al. Chem. Rev.; 2015; 115, 12491-12545. (Year: 2015).*
Mitsunobu et al. The Journal of Biological Chemistry; 2014; vol. 289, No. 9, pp. 5860-5875). (Year: 2014).*
"Flap endonucleases" from Wikipedia. Printed on Sep. 14, 2023.*
"Exonucleases" from Wikipedia. Printed on Sep. 14, 2023.*
"Thermostable FEN1". pp. 1-3. Printed on Jan. 20, 2024.*
Amado, et al. Wild-type KRAS is required for panitumumab efficacy in patients with metastic colorectal cancer. Journal of Clinical Oncology. Apr 1, 2008; 26(10); 1626-1634.
Awuah, et al. Thermal inactivation kinetics of trypsin at aseptic processing temperatures. Journal of food process engineering 1993 v.16 No. 4 pp. 315-328 (abstract).
BLAST. Basic local alignment search tool. Available at http://blast.ncbi.nlm.nih.gov/Blast.cgi. Accessed on Oct. 10, 2016.
Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.
Brenner. A cultivated taste for yeast. Genome Biol. 2000;1(1):Reviews103. Epub Apr. 27, 2000.
Brenner, C. Chemical genomics in yeast. Genome Biology. 2004; 5:240.

(56) References Cited

OTHER PUBLICATIONS

Brietbach et al. Direct Quantification of Cell-Free, Circulating DNA from Unpurified Plasma. PLoS One 9(3):1-11 (2014).
Co-pending U.S. Appl. No. 16/368,355, filed Mar. 28, 2019.
Creating Standard Curves with Genomic DNA or Plasmid DNA Templates for Use in Quantitative PCR. Applied Biosystems 2003. Downloaded Oct. 17, 2017. URL: <http://www6.appliedbiosystems.com/support/tutorials/pdf/quant_pcr.pdf>.
Dawson, et al., Analysis of circulating tumor DNA to monitor metastatic breast cancer. The New England Journal of Medicine. Mar. 28, 2013. 368(13); 1199-1209.
Delcher, et al. Alignment of whole genomes. Nucleic Acids Research. Feb. 2, 1999; 27(11): 2369-2376.
Devonshire, Alison S. et al. Towards standardisation of cell-free DNA measurement in plasma: controls for extraction efficiency, fragment size bias and quantification, Analytical and Bioanalytical Chemistry, 406(26): 6499-6512 (2014).
Dicker, et al. The detection of TP53 mutations in chronic lymphocytic leukemia independently predicts rapid disease progression and is highly correlated with a complex aberrant karyotype. Leukemia. Jan. 2009; 23(1):117-124.
Eason, et al. Characterization of synthetic DNA bar codes in *Saccharomyces cerevisiae* gene-deletion strains. Proc Natl Acad Sci U S A. Jul. 27, 2004; 101(30): 11046-11051.
EMBOSS. EMBOSS Water: Pairwise Sequence Alignment (Nucleotide). Available at http://www.ebi.ac.uk/Tools/psa/emboss_water/nucleotide.html. Accessed on Oct. 10, 2016.
Enari et al. A caspase-activated DNase that degrades DNA during apoptosis, and its inhibitor ICAD. Nature 391:43-50 (1998).
Florsheim, et al. Integrated Innate Mechanisms Involved in Airway Allergic Inflammation to the Serine Protease Subtilisin. J Immunol. May 15, 2015; 194(10): 4621-4630.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Freshney. Culture of Animal Cells: A Manual of Basic Technique and Specialized Applications. 6th Edition. 2010.
Giacona, et al. Cell-free DNA in human blood plasma: length measurements in patients with pancreatic cancer and healthy controls. Pancreas. Jul. 1998;17(1):89-97.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
Guatelli et al. Isothermal, in vitro amplification of nucleic acids by a multienzyme reaction modeled after retroviral replication. PNAS USA 87(5):1874-1878 (1990).
Harkins, et al., Replicating fetal trisomy patient-like reference material for use in non-invasive prenatal screening tests. Sera Care. AMP 2015. Nov. 5-7, 2015.
Harlow, et al. Antibodies: A Laboratory manual. Cold Spring Harbor Laboratory. 1988.
Heinrich et al. Kinase mutations and imatinib response in patients with metastatic gastrointestinal stromal tumor. Journal of Clinical Oncology. Dec. 1, 2003; 21(23): 4342-4349.
Horizon Product Specification. cfDNA Reference Standard Set. 6068PSS-01(V-01). 2015.
Hussmann, et al. Reply to Schmitt et al.: Data-filtering schemes for avoiding double-counting in circle sequencing. PNAS. Apr. 22, 2014; 111(16).
Illumina. Genome Analyzer System. Available at http://support.illumina.com/content/dam/illumina-marketing/documents/products/datasheets/datasheet_genome_analyzeriix.pdf. Accessed on Oct. 10, 2016.
Jahr, et al. DNA fragments in the blood plasma of cancer patients: quantitations and evidence for their origin from apoptotic and necrotic cells. Cancer Res. Feb. 15, 2001;61(4):1659-65.
Jeffreys et al. DNA Enrichment by Allele-Specific Hybridization (Deash): A Novel Method for Haplotyping and for Detecting Low-Frequency Base Substitutional Variants and Recombinant DNA Molecules. Genome Research 13:2316-2324 (2003).
Jiang et al. The Long and Short of Circulating Cell-Free DNA and the Ins and Outs of Molecular Diagnostics. Trends Genet 32(6):360-371 (2016).
Katayama, et al. Mechanisms of acquired crizotinib resistance in ALK-rearranged lung cancers. Sci. Transl Med. Feb. 8, 2012; 8(4).
Kent, W.J. Blat-The Blast-like alignment tool. Genome Research. 2012: 656-664.
Kumar, et al. Emerging technologies in yeast genomics. Nat Rev Genet. Apr. 2001;2(4):302-12.
Kurtz, et al. Versatile and open software for comparing large genomes. Biomed central. Jan. 30, 2004.
Landegren, U. Molecular mechanics of nucleic acid sequence amplification. Elsevier Science. Jun. 1993. 9(6). 199-204.
Langmead et al. Ultrafast and memory-efficient alignment of short DNA sequences to the human genome. Genome biology 10:R25 (10 pgs) (2009).
Larking, et al. Clustal W and Clustal X version 2.0. Bioinformatics applications note. 2007. 2947-2948; 23(21).
Lee, et al. Nucleic acid amplification technologies: application to disease diagnosis. Biotechniques books. 1997.
Li, et al. Fast and accurate long-read alignment with burrows-wheeler transform. Bioinformatics. Mar. 1, 2010;26(5):589-95.
Li et al. Fast and accurate short read alignment with burrows-wheeler transform. Bioinformatics 25(14):1754-1760 (2009).
Li, et al. Technical advance: Whole genome amplification of plasma-circulating DNA enables expanded screening for allelic imbalance in plasma. Journal of Molecular Diagnostics. Feb. 2006. 8(1); 22-30.
Lin, et al. Rolling Circle Enzymatic Replication of a Complex Multi-Crossover DNA Nanostructure. J Am Chem Soc. Nov. 21, 2007; 129(46): 14475-14481.
Lipman, et al. Rapid and sensitive protein similarity searches. Science. Mar. 22, 1985; 227(4693):1435-41.
Lizardi, et al. Exponential amplification of recombinant-RNA hybridization probes. Biotechnology. 1988. 6:1197-1202.
Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.
Lou et al., Supporting Information for "High-throughput DNA sequencing errors are reduced by orders of magnitude using circle sequencing," Proc Natl Acad Sci U S A., 110(49): 19872-7. doi: 10.1073/pnas.1319590110 (14 pages) (2013).
Lou et al. BioTechniques, pp. 1-14 [Support Information to Lou et al. BioTechniques 110(49) publication] (2013).
Maldonado, et al. Determinants of BRAF mutations in primary melanomas. Journal of the National Cancer Institute. Dec. 17, 2003; 95(24):1878-1880.
Matta, et al. Isolation and partial characterization of a thermostable extracellular protease of Bacillus polymyxa B-17. Int J Food Microbiol. Jul. 21, 1998;42(3):139-45 (abstract).
McLendon, et al. Survival analysis of presumptive prognostic markers among oligodendrogliomas. John Wiley & Sons. Oct. 15, 2005; 104(8):1693-1699.
McPherson, et al. eds. PCR 2: a practical approach. Oxford University Press. 1995.
Miller, et al. A simple salting out procedure for extracting DNA from human nucleated cells. Nucleic Acid Research. 1988; 16(3).
Misale, et al. Emergence of KRAS mutations and acquired resistance to anti-EGFR therapy in colorectal cancer. Nature. Jun. 13, 2012; 486(7404):532-536.
Neumann, et al., Frequency and type of KRAS mutations in routine diagnostic analysis of metastatic colorectal cancer. Pathol Res Pract. 2009;205(12):858-62.
Novocraft Technologies SDN BHD. NovoAlign. Available at http://www.novocraft.com/products/novoalign/. Accessed on Oct. 10, 2016.
Olivier, et al., TP53 mutations in human cancers: origins, consequences, and clinical use. Cold Spring Harb. Perspect Biology. 2010;1-17.

(56) References Cited

OTHER PUBLICATIONS

Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.
Paska et al. Effect of formalin, acetone, and RNAlater fixatives on tissue preservation and different size amplicons by real-time PCR from paraffin-embedded tissue. Diagn Mol Path 13(4):234-240 (2004).
PCT/US2016/064853 International Search Report and Written Opinion dated Feb. 7, 2017.
Pearson, et al. Improved Tools for Biological Sequence Comparison. Proc. Nat'l Acad. Sci. USA. 85 (1988): 2444-48.
Polidoros et al. Rolling circle amplification-RACE: a method for simultaneous isolation of 5' and 3' cDNA ends from amplified cDNA templates. BioTechniques 41:35-42 (2006).
Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.
Qiagen. How can QIAGEN Protease and Proteinase K be inactivated? Available at https://www.qiagen.com/ca/resources/faq?id=d24681d7-88e7-421a-84d9-27bfd5141103&lang=en. Accessed Apr. 11, 2018.
Remacle, et al. Substrate Cleavage Analysis of Furin and Related Proprotein Convertases—A Comparative Study. J Biol Chem. Jul. 25, 2008; 283(30): 20897-20906.
Samuels, et al. High Frequency of Mutations of the PIK3CA Gene in Human Cancers. Science Mag. Apr. 23, 2004; 304.
Schmitt, et al. Risks of double-counting in deep sequencing. PNAS. Apr. 22, 2014;111(16).
SeraCare and NIST Partner on Development of Circulating Tumor DNA Reference Standards for Diagnostics (Press Release). SeraCare Life Sciences, Inc. Jul. 14, 2016 (2 pages).
Seraseq(TM) ctDNA: A Breakthrough QC Technology. SeraCare Life Sciences, Inc. (2017) 6 pages.
Shaw, et al. Clinical Features and Outcome of Patients With Non-Small-Cell Lung Cancer Who Harbor EML4-ALK. Journal of Clinical Oncology. Sep. 10, 2009; 27(26):4247-4253.
Sievers, et al. Fast, Scalable generation of high-quality protein multiple sequence alignments using clustal omega. Molecular systems biology. 2011.
Sigma-Alorich. Protease from Streptomyces griseus. Available at https://www.sigmaaldrich.com/catalog/product/sigma/p6911?lang=en&region=US#. Accessed Apr. 11, 2018.
Slater, et al. Automated generation of heuristics for biological sequence comparison. BMC Bioinformatics. Feb. 15, 2005; 6(31): 1-11.
SOAP.Short Oligonucleotide Analysis Package. Available at http://soap.genomics.org.cn/. Accessed on Oct. 10, 2016.
SOURCEFORGE-Maq-Mapping-and-Assembly-with-Qualities. Available at http://maq.sourceforge.net/. Accessed on Oct. 10, 2016.
Spargo, et al. Detection of *M. tuberculosis* DNA using thermophilic strand displacement amplification. Mol Cell Probes. Aug. 1996;10(4):247-56.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology: Hybridization with nucleic acid probes. Elsevier Science. 1993.
U.S. Appl. No. 15/102,241 Office Action dated Oct. 12, 2018.
U.S. Appl. No. 15/800,558 Office Action dated Jan. 26, 2018.
U.S. Appl. No. 15/800,558 Final Office Action dated Jul. 6, 2018.
Walsh, et al. Chelex 100 as a medium for simple extraction of DNA for PCR-based typing from forensic material. BioTechniques. 1991;10(4):506-513.
Wang, et al., Using ultra-sensitive next generation sequencing to dissect DNA damage-induced mutagenesis. Nature:Scientific Report. Dec. 2015.6:25310.
Wharam, et al. Specific detection of DNA and RNA targets using a novel isothermal nucleic acid amplification assay based on the formation of a three-way junction structure. Nucleic Acids Res. Jun. 1, 2001; 29(11): e54.
Widlak et al. Cleavage Preferences of the Apoptotic Endonuclease DFF40 (Caspase- activated DNase or Nuclease) on Naked DNA and Chromatin Substrates. The Journal of Biological Chemistry 275:8226-8232 (2000).
Winzeler, et al. Functional Characterization of the *S. cerevisiae* Genome by Gene Deletion and Parallel Analysis. Science. Aug. 6, 1999: vol. 285, Issue 5429, pp. 901-906.
European Patent Application No. 16871682.7 Extended European Search Report dated Jul. 26, 2019.
Kurtz, et al. Versatile and open software for comparing large genomes. Genome Biol. 2004;5(2):R12. doi: 10.1186/GB-2004-5-2-r12. Epub Jan. 30, 2004.
Li et al. Fast and accurate short read alignment with Burrows-Wheeler transform. Bioinformatics 25:1754-60 (2009).
PCT/US2019/036608 International Search Report and Written Opinion dated Sep. 23, 2019.
Ali et al., Rolling circle amplification: a versatile tool for chemical biology, materials science and medicine. Chem Soc Rev 43(10): 3324-3341 (2014).
Beck, et al. Next generation sequencing of serum circulating nucleic acids from patients with invasive ductal breast cancer reveals differences to healthy and nonmalignant controls. Mol Cancer Res. Mar. 2010;8(3):335-42. doi: 10.1158/1541-7786.MCR-09-0314. Epub Mar. 9, 2010.
Dean et al., Comprehensive human genome amplification using multiple displacement amplification. Proc Natl Acad Sci USA 99(8): 5261-5266 (2002).
Hindson, et al. High-throughput droplet digital PCR system for absolute quantitation of DNA copy number. Analytical Chemistry. 83(22):8604-8610 (2011).
Moran et al., Heat-labile proteases in molecular biology applications. FEMS Microbiology Letters 197(1): 59-63 (2001).
Newman, et al. An ultrasensitive method for quantitating circulating tumor DNA with broad patient coverage. Nat Med. May 2014;20(5):548-54. Epub Apr. 6, 2014.
Pinheiro et al., Evaluation of a Droplet Digital Polymerase Chain Reaction Format for DNA Copy Number Quantification. Analytical Chemistry. 84(2):1003-1011 (2012).
Schmitt et al., Detection of ultra-rare mutations by next-generation sequencing. PNAS. 109(36):14508-14523 (2012).
U.S. Appl. No. 16/434,941 Final Office Action dated Apr. 16, 2021.
U.S. Appl. No. 16/434,941 Non-Final Office Action dated Sep. 8, 2020.
U.S. Appl. No. 16/689,018 Non-Final Office Action dated Dec. 24, 2021.
U.S. Appl. No. 16/945,553 Non-Final Office Action dated Dec. 22, 2021.
U.S. Appl. No. 16/434,941 Final Office Action dated Mar. 10, 2020.
U.S. Appl. No. 16/434,941 Office Action dated Nov. 25, 2019.
U.S. Appl. No. 15/102,241 Office Action dated Apr. 25, 2019.
U.S. Appl. No. 15/947,100 Office Action dated Oct. 24, 2019.
Wang et al., DNA amplification method tolerant to sample degradation. Genome Research. 14(11):2357-2366 (2004).
Yan, et al. Isothermal amplified detection of DNA and RNA. Mol Biosyst. May 2014;10(5):970-1003.
Dean, et al. Rapid amplification of plasmid and phage DNA using phi29 DNA polymerase and multiply-primed rolling circle amplification. Genome Research 11.6 ( 2001): 1095-1099.
Dillon L.W. et al. Production of Extrachromosomal MicroDNAs Is Linked to Mismatch Repair Pathways and Transcriptional Activity. Cell Rep. Jun. 23, 2015;11(11):1749-59.
EMBOSS. EMBOSS Needle: Pairwise Sequence Alignment (NUCLEOTIDE). Available at http://www.ebi.ac.uk/Tools/psa/emboss_needle/nucleotide.html. Accessed on Oct. 10, 2016.
Faham M. et al. Deep-sequencing approach for minimal residual disease detection in acute lymphoblastic leukemia. Blood. Dec. 20, 2012;120(26):5173-80.
Huang, S.H. Inverse polymerase chain reaction. An efficient approach to cloning cDNA ends. Mol Biotechnol. Aug. 1994;2(1):15-22.

(56) References Cited

OTHER PUBLICATIONS

Kroenlein H. et al. Molecular analysis of the t(2;8)/MYC-IGK translocation in high-grade lymphoma/leukemia by long-distance inverse PCR. Genes Chromosomes Cancer. Mar. 2012;51(3):290-9.

Kumar P. Normal and Cancerous Tissues Release Extrachromosomal Circular DNA (eccDNA) into the Circulation. Mol Cancer Res. Sep. 2017;15(9):1197-1205.

Li Y. et al. Isothermally sensitive detection of serum circulating miRNAs for lung cancer diagnosis. Anal Chem. Dec. 3, 2013;85(23):11174-9.

Liu W.H. et al. Inverse PCR-based RFLP scanning identifies low-level mutation signatures in colon cells and tumors. Cancer Res. Apr. 1, 2004;64(7):2544-51.

Mitchell, et al. Circulating microRNAs as stable blood-based markers for cancer detection. Proc Natl Acad Sci USA 105, 10513-8 (2008). Proceedings of the National Academy of Sciences, Jul. 29, 2008.

Nelson J.R. et al. TempliPhi, phi29 DNA polymerase based rolling circle amplification of templates for DNA sequencing. Biotechniques. Jun. 2002;Suppl:44-7. PMID: 12083397.

Ochman, et al. Genetic applications of an inverse polymerase chain reaction. Genetics. Nov. 1988;120(3):621-3.

Pavlopoulos A. Identification of DNA sequences that flank a known region by inverse PCR. Methods Mol Biol. 2011; 772:267-75.

Schubert J. et al. Surveying cereal-infecting geminiviruses in Germany—diagnostics and direct sequencing using rolling circle amplification. Virus Res. Jul. 2007;127(1):61-70.

Shibata Y. et al. Extrachromosomal microDNAs and chromosomal microdeletions in normal tissues. Science. Apr. 6, 2012;336(6077):82-6. doi: 10.1126/science.1213307. Epub Mar. 8, 2012. Erratum in: Science. Jun. 22, 2012;336(6088):1506.

Tsaftaris A. et al. Rolling circle amplification of genomic templates for inverse PCR (RCA-GIP): a method for 5'-and 3'-genome walking without anchoring. Biotechnol Lett. Jan. 2010;32(1):157-61.

U.S. Appl. No. 16/927,898 Non-Final Office Action dated Mar. 9, 2022.

Zhang et al., "Amplification of target-specific, ligation-dependent circular probe" Gene (1998) 211:277-285.

Bevan, et al., Sequencing of PCR-amplified Dna, Pcr methods and applications, 1992; vol. 1: 222-228.

Jensen Tj et al., Noninvasive detection of a balanced fetal translocation from maternal plasma. Clin Chem. Oct. 2014;60(10):1298-305. Epub Jul. 16, 2014.

PCT/US2016/064853 International Search Report with Written Opinion dated Feb. 7, 2017.

Co-pending U.S. Appl. No. 18/164,439, inventors Lin; Shengrong et al., filed on Feb. 3, 2023.

Mo et al., Cell-free Circulating miRNA Biomarkers in Cancer. Journal of Cancer, 3:432-448 (2012).

Gansauge et al. Single-Stranded DNA Library Preparation from Highly Degraded DNA Using T4 DNA Ligase. Nucleic Acids Research 45(10):e79 [1-10] (Jan. 2017).

Van Nieuwerburgh et al., Quantitative bias in Illumina truseq and a novel post amplification barcoding strategy for multiplexed DNA and small RNA deep sequencing. PLoS ONE 6(10):e26969, and Supplementary Materials and Methods (2011).

\* cited by examiner

| Lane | Sample |
|---|---|
| 1 | No DNA (negative control) |
| 2 | Target DNA with 0 base 5' flap |
| 3 | Target DNA with 10 base 5' flap |
| 4 | Target DNA with 17 base 5' flap |

METHODS AND COMPOSITIONS FOR FORMING LIGATION PRODUCTS

CROSS-REFERENCE

This application is a U.S. National Stage entry of International Application No. PCT/US2016/064853, filed Dec. 2, 2016, which claims the benefit of U.S. Provisional Application No. 62/262,883 filed on Dec. 3, 2015, each of which is herein incorporated by reference in its entirety.

BACKGROUND OF THE INVENTION

Forming polynucleotide ligation products can have a variety of uses, such as examining target polynucleotides, molecular cloning methods to generate expression vectors, cDNA library construction, and as a pre-step to amplification and sequencing reactions. Ligation products can be formed from both double-stranded nucleic acids and single-stranded nucleic acids. Double-stranded nucleic acids can be ligated by "sticky end" ligation or "blunt end" ligation. In sticky end ligation, staggered ends comprising terminal overhangs can hybridize to a ligation partner. In blunt end ligation, terminal overhangs are not present and successful ligation depends on transient associations of 5' ends and 3' ends. Blunt end ligations in general are less efficient than sticky end ligations, and various optimizations, such as adjusting concentrations, incubation times, and temperatures, can be applied to improve efficiencies. Single-stranded polynucleotides can also be ligated. However, efficient ways of carrying out this reaction are lacking. Existing single-stranded DNA ligation methods can suffer from slow kinetics, poor yield, and severe nucleotide preference.

SUMMARY OF THE INVENTION

In view of the foregoing, there is a need for improved efficiency in the generation of ligation products with single-stranded polynucleotide targets. The methods and compositions of the present disclosure address this need, and provide additional advantages as well.

In an aspect, the present disclosure provides a method for identifying a sequence variant in a nucleic acid sample comprising a plurality of cell-free DNA polynucleotides. In some embodiments, the method comprises (a) forming a plurality of ligation products, wherein an individual member of the ligation products is formed by ligating a cell-free DNA polynucleotide to a single-stranded adaptor of a polynucleotide complex, wherein the polynucleotide complex comprises a first segment of a capture probe hybridized to a cell-free DNA polynucleotide and a second segment of the capture probe hybridized to a single-stranded adaptor, wherein an individual adaptor comprises a unique barcode sequence; (b) circularizing the plurality of ligation products to yield a plurality of circular target polynucleotides; (c) generating a plurality of concatemers, wherein an individual concatemer of the plurality is formed via extension of a first primer that hybridizes to a target polynucleotide via sequence complementarity; (d) generating a plurality of extension products from the concatemers, wherein an individual extension product of the plurality is formed via extension of a second primer that hybridizes to a concatemer via sequence complementarity; (e) sequencing a plurality of the extension products to produce sequencing reads; and (f) identifying a sequence difference between sequencing reads and a reference sequence as the sequence variant, when (i) the sequence difference is detected in a sequencing read of an extension product containing at least two occurrences of the sequence difference, and (ii) the sequence difference occurs in at least two different sequencing reads having distinct barcode sequences.

In an aspect, a method for identifying a sequence variant in a nucleic acid sample comprising a plurality of cell-free DNA polynucleotides comprises (a) forming a plurality of ligation products, wherein an individual member of the ligation products is formed by ligating a cell-free DNA polynucleotide to a single-stranded adaptor of a polynucleotide complex, wherein the polynucleotide complex comprises a first segment of a capture probe hybridized to a cell-free DNA polynucleotide and a second segment of the capture probe hybridized to a single-stranded adaptor; (b) circularizing the plurality of ligation products to yield a plurality of circular target polynucleotides, wherein an individual circular target polynucleotide comprises (i) a first junction between a 5' end of a cell-free DNA polynucleotide and a 3' end of a single-stranded adaptor and (ii) a second junction between a 3' end of the cell-free DNA polynucleotide and a 5' end of the single-stranded adaptor; (c) generating a plurality of concatemers, wherein an individual concatemer of the plurality is formed via extension of a first primer that hybridizes to a target polynucleotide via sequence complementarity; (d) generating a plurality of extension products from the concatemers, wherein an individual extension product of the plurality is formed via extension of a second primer that hybridizes to the concatemer via sequence complementarity; (e) sequencing a plurality of the extension products to produce sequencing reads; (f) identifying a sequence difference between sequencing reads and a reference sequence as the sequence variant, when (i) the sequence difference is detected in a sequencing read of an extension product containing at least two occurrences of the sequence difference, and (ii) the sequence difference occurs in at least two different sequencing reads having distinct first and second junctions.

In some embodiments, a method for identifying a sequence variant disclosed herein comprises degrading the capture probe prior to circularizing in (b). In some embodiments, degrading the capture probe comprises degrading the capture probe enzymatically. In some embodiments, degrading the capture probe enzymatically is effected by an endonuclease.

In some embodiments, the capture probe comprises a tag. In some embodiments, a method for identifying a sequence variant further comprises isolating the polynucleotide complex by immobilizing it directly or indirectly to a support comprising a selective binding agent that specifically binds the tag. In some embodiments, the isolating takes place prior to step (c). In some embodiments, the support comprises a magnetic bead.

In some embodiments, the sequence variant comprises at least one of a single nucleotide polymorphism, a single nucleotide variant, an insertion, a deletion, a duplication, an inversion, a translocation, a copy number variation, a gene fusion, and a mutation indicative of methylation.

In some embodiments, a method for identifying a sequence variant disclosed herein comprises contacting the ligation product with bisulfite to modify unmethylated cytosine in the ligation product to uridine. In some embodiments, the sequence variant comprises a C to T mutation.

In some embodiments, the first primer comprises a first 5' end that does not hybridize to the target polynucleotide via sequence complementarity. In some embodiments, the second primer comprises a second 5' end that does not hybridize to the concatemer via sequence complementarity. In some embodiments, a method for identifying a sequence variant further comprises amplifying the plurality of extension products of (d) using a third primer comprising a sequence of at least a portion of the first 5' end and a fourth primer comprising a sequence of at least a portion of the second 5' end.

In some embodiments, the first primer hybridizes to a sequence of at least a segment of the cell-free DNA polynucleotide. In some embodiments, the first primer comprises a gene specific sequence. In some embodiments, the first primer comprises a random sequence. In some embodiments, the second primer hybridizes to a sequence complementary to at least a segment of the cell-free DNA polynucleotide. In some embodiments, the second primer comprises a gene specific sequence. In some embodiments, the second primer comprises a random sequence.

In some embodiments, the first primer hybridizes to a sequence of at least a segment of the single-stranded adaptor. In some embodiments, the second primer hybridizes to a sequence complementary to at least a segment of the single-stranded adaptor.

In some embodiments, the first primer comprises a barcode sequence. In some embodiments, the second primer comprises a barcode sequence.

In some embodiments, the capture probe comprises a double-stranded nucleic acid, and prior to forming a polynucleotide complex, the double-stranded nucleic acid is separated into two single-stranded capture probes.

In some embodiments, the cell-free DNA is extended to fill in a sequence gap between the cell-free DNA polynucleotide and the single-stranded adaptor using the capture probe as a template prior to or concurrent with said ligating of (a). In some embodiments, the single-stranded adaptor is extended to fill in a sequence gap between the cell-free DNA polynucleotide and the single-stranded adaptor using the capture probe as a template prior to or concurrent with said ligating of (a).

In some embodiments, the cell-free DNA polynucleotide comprises at a 5' end a segment lacking sequence complementarity to the capture probe. In some embodiments, the method further comprises cleaving the segment of the cell-free DNA polynucleotide lacking sequence complementarity to the capture probe with an endonuclease prior to or concurrent with said ligating of (a).

In some embodiments, the cell-free DNA polynucleotide comprises at a 3' end a segment lacking sequence complementarity to the capture probe. In some embodiments, the method comprises cleaving the segment of the cell-free DNA polynucleotide lacking sequence complementarity to the capture probe with an endonuclease prior to or concurrent with said ligating of (a).

In an aspect, the present disclosure provides a method for amplifying cell-free DNA comprising (a) forming a ligation product by ligating a cell-free DNA polynucleotide to a single-stranded adaptor of a polynucleotide complex, wherein the polynucleotide complex comprises a first segment of a capture probe hybridized to a cell-free DNA polynucleotide and a second segment of the capture probe hybridized to a single-stranded adaptor; (b) degrading or selectively removing the capture probe; (c) circularizing the ligation product to yield a circular target polynucleotide; (d) generating a concatemer comprising a single-stranded polynucleotide from the circular target polynucleotide by extension of a first primer that hybridizes to the target polynucleotide via sequence complementarity; and (e) generating a plurality of extension products containing one or more copies of the target polynucleotide by extension of a second primer that hybridizes to the concatemer via sequence complementarity.

In some embodiments, the first primer comprises a first 5' end that does not hybridize to the target polynucleotide via sequence complementarity. In some embodiments, the second primer comprises a second 5' end that does not hybridize to the concatemer via sequence complementarity. In some embodiments, the method further comprises amplifying the plurality of extension products of (d) using a third primer comprising a sequence of at least a portion of the first 5' end and a fourth primer comprising a sequence of at least a portion of the second 5' end.

In some embodiments, the first primer hybridizes to a sequence of at least a segment of the cell-free DNA polynucleotide. In some embodiments, the first primer comprises a gene specific sequence. In some embodiments, the first primer comprises a random sequence. In some embodiments, the second primer hybridizes to a sequence complementary to at least a segment of the cell-free DNA polynucleotide. In some embodiments, the second primer comprises a gene specific sequence. In some embodiments, the second primer comprises a random sequence.

In some embodiments, the first primer hybridizes to a sequence of at least a segment the single-stranded adaptor. In some embodiments, the second primer hybridizes to a sequence complementary to at least a segment of the single-stranded adaptor.

In some embodiments, the first primer comprises a barcode sequence. In some embodiments, the second primer comprises a barcode sequence.

In some embodiments, the capture probe comprises a double-stranded nucleic acid, and prior to forming a polynucleotide complex, the double-stranded nucleic acid is separated into two single-stranded capture probes.

In an aspect, the present disclosure provides a method of conducting rolling circle amplification comprising (a) providing a circular polynucleotide comprising a target polynucleotide, wherein the circular polynucleotide is formed by: (i) mixing a cell-free DNA polynucleotide and a single-stranded adaptor with a capture probe to form a polynucleotide complex, wherein a first segment of the capture probe hybridizes with the cell-free DNA polynucleotide via sequence complementarity and a second segment of the capture probe hybridizes with the single-stranded adaptor via sequence complementarity; (ii) ligating the cell-free DNA polynucleotide to the single-stranded adaptor of a polynucleotide complex, thereby forming a ligation product; (iii) degrading or selectively removing the capture probe; and (iv) circularizing the ligation product to yield the circular target polynucleotide; (b) subjecting an amplification reaction mixture to multiple cycles of rolling circle amplification to generate a plurality of amplification products comprising concatemers, wherein the amplification reaction mixture comprises (i) a polymerase having strand displacement activity, (ii) the circular target polynucleotide of (a), and (iii) primers; wherein each cycle of the multiple cycles of rolling circle amplification comprises denaturation at a denaturing temperature, primer annealing at an annealing temperature, and primer elongation at an elongation temperature for a given elongation time period, to generate the plurality of amplification products comprising concatemers; and wherein the plurality of amplification products generated is characterized in that it contains a higher proportion of con catemers having at least two copies of the target polynucleotide as compared to a plurality of amplification products generated by utilizing one cycle of amplification under comparable conditions for denaturation and primer annealing but with an elongation time period comparable to a sum of the elongation time period of the multiple cycles.

In one aspect, the present disclosure provides a method for forming a ligation product of a first singled-stranded polynucleotide and a second single-stranded polynucleotide using a capture probe. In some embodiments, the method comprises: (a) mixing the first single-stranded polynucleotide and the second single-stranded polynucleotide with the capture probe to form a complex of polynucleotides wherein a first segment of the capture probe specifically hybridizes with the first single-stranded polynucleotide via sequence complementarity and a second segment of the capture probe specifically hybridizes with the second single-stranded polynucleotide via sequence complementarity; (b) ligating the first single-stranded polynucleotide to the second single-stranded polynucleotide, thereby forming the ligation product; and (c) degrading or selectively removing the capture probe. In some embodiments, step (c) comprises degrading the capture probe enzymatically. In some embodiments, the degradation is effected by an endonuclease. In some embodiments, the capture probe comprises a tag. In some embodiments, step (c) comprises selectively removing the capture probe with a binding element that selectively binds the tag. In some embodiments, the tag is biotin. In some embodiments, the first single-stranded polynucleotide comprises from a 5' end to a 3' end a first segment, a second segment, and a third segment wherein the first and second segments do not specifically hybridize to the capture probe via sequence complementarity and the third segment specifically hybridizes to the capture probe via sequence complementarity. In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality. In some embodiments, the barcode sequence of each first single-stranded polynucleotide in a single reaction is different from every other barcode sequence. In some embodiments, the barcode sequence is uniquely associated with a single ligation reaction in a plurality of ligation reactions. In some embodiments, the method comprises amplifying the ligation product or a segment of the ligation product using a first primer that specifically hybridizes to the first or the second segment of the first single-stranded polynucleotide, or a complement thereof, via sequence complementarity. In some embodiments, the first primer comprises at a 5' end a first sequencing adaptor lacking sequence complementarity to the ligation product, or a complement thereof. In some embodiments, (i) the first primer specifically hybridizes to the first segment of the first single-stranded polynucleotide, (ii) the first segment of the first single-stranded polynucleotide comprises a sequence common to a plurality of different first single-stranded polynucleotides, and (iii) the second segment of the first single-stranded polynucleotide comprises a barcode sequence that is not the same for all first single-stranded polynucleotides in the plurality. In some embodiments, the ligation product or a segment of the ligation product is amplified using a second primer that specifically hybridizes to an extension product of the first primer via sequence complementarity. In some embodiments, the second primer comprises at a 5' end a second sequencing adaptor lacking sequence complementarity to the extension product of the first primer. In some embodiments, the first single-stranded polynucleotide is extended to fill in a sequence gap between the first single-stranded polynucleotide and the second single-stranded polynucleotide using the capture probe as a template prior to or concurrent with step (b). In some embodiments, the second single-stranded polynucleotide comprises at a 5' end a segment lacking sequence complementarity to the capture probe. In some embodiments, the method comprises cleaving the segment of the second single-stranded polynucleotide lacking sequence complementarity to the capture probe with an endonuclease prior to or concurrent with step (b). In some embodiments, at least one of the first or second single-stranded polynucleotides is a cell-free polynucleotide. In some embodiments, step (a) comprises mixing the first single-stranded polynucleotide, the second single-stranded polynucleotide, and the capture probe with a blocking polynucleotide that hybridizes to a sequence variant via sequence complementarity, wherein the sequence variant is at least 90% identical and less than 100% identical to the second single-stranded polynucleotide.

In one aspect, the present disclosure provides a reaction mixture for forming a ligation product comprising a first singled-stranded polynucleotide and a second single-stranded polynucleotide using a capture probe. In some embodiments, the reaction mixture comprises: (a) a mixture of the first single-stranded polynucleotide, the second single-stranded polynucleotide, and the capture probe wherein a first segment of the capture probe specifically hybridizes with the first single-stranded polynucleotide via sequence complementarity and a second segment of the capture probe specifically hybridizes with the second single-stranded polynucleotide via sequence complementarity; and (b) a ligase to effect the ligation of the first single-stranded polynucleotide and the second single-stranded polynucleotide, wherein (i) the capture probe comprises RNA and the first and second single-stranded polynucleotides comprise DNA, (ii) the capture probe comprises deoxyuridine, or (iii) the capture probe comprises a tag that selectively binds to a binding element. In some embodiments, the capture probe comprises deoxyuridine. In some embodiments, the capture probe comprises a tag that selectively binds to a binding element. In some embodiments, the tag is biotin. In some embodiments, the reaction mixture comprises a polymerase. In some embodiments, the polymerase extends the first single-stranded polynucleotide to fill in a sequence gap between the first single-stranded polynucleotide and the second single-stranded polynucleotide using the capture probe as a template. In some embodiments, the reaction mixture comprises an endonuclease. In some embodiments, the endonuclease cleaves a segment of the second single-stranded polynucleotide lacking sequence complementarity to the capture probe. In some embodiments, the endonuclease is a flap endonuclease. In some embodiments, the reaction mixture is contained in a container. In some embodiments, the container is a well, a plate, a tube, a chamber, a flow cell, or a chip. In some embodiments, the first single-stranded polynucleotide comprises from a 5' end to a 3' end a first segment, a second segment, and a third segment wherein the first and second segments do not specifically hybridize to the capture probe via sequence complementarity and the third segment specifically hybridizes to the capture probe via sequence complementarity. In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality. In some embodiments, a reaction comprises at least 200 different first single-stranded polynucleotides, each having a different barcode sequence. In some embodiments, the barcode sequence of each first single-stranded polynucleotide is different from every other barcode sequence in the reaction mixture. In some embodiments, the barcode sequence is uniquely associated with a single ligation reaction in a plurality of ligation reactions. In some embodiments, the first single-stranded polynucleotide or the second single-stranded polynucleotide is a cell-free polynucleotide. In some embodiments, the reaction mixture comprises a blocking polynucleotide that hybridizes to a sequence variant via sequence complementarity, wherein the sequence variant is at least 90% identical and less than 100% identical to the second single-stranded polynucleotide.

In one aspect, the present disclosure provides a kit for capturing single-stranded target polynucleotides. In some embodiments, the kit comprises a plurality of capture probes, one or more first single-stranded polynucleotides, and instructions for using the plurality of capture probes for capturing one or more single-stranded target polynucleotides. In some embodiments, a capture probe comprises at a 5'end a segment exhibiting sequence complementarity to a first single-stranded polynucleotide and at a 3'end a second segment exhibiting sequence complementarity to a single-stranded target polynucleotide. In some embodiments, the single-stranded target polynucleotide is a cell-free target polynucleotide. In some embodiments, the capture probe comprises at least 10 deoxyuridines. In some embodiments, the one or more first single-stranded polynucleotides comprise from a 5' end to a 3' end a first, a second, and a third segment wherein the first and second segments do not specifically hybridize to the capture probe via sequence complementarity and the third segment specifically hybridizes to the capture probe via sequence complementarity. In some embodiments, (i) the first segment of each first single-stranded polynucleotide comprises a sequence common to a plurality of different first single-stranded polynucleotides, and (ii) the second segment of each first single-stranded polynucleotide comprises a barcode sequence that is not the same for all first single-stranded polynucleotides in the plurality. In some embodiments, the kit comprises one or more first primers comprising a 3' end sequence that specifically hybridizes to the first or the second segment of the first single-stranded polynucleotide via sequence complementarity. In some embodiments, the one or more first primers comprise, at a 5' end, a first sequencing adaptor lacking sequence complementarity to the first polynucleotide. In some embodiments, the kit comprises one or more second primers comprising a 3' end sequence that specifically hybridize to extension products of the one or more first primers via sequence complementarity. In some embodiments, the one or more second primers comprise, at a 5' end, a second sequencing adaptor lacking sequence complementarity to the extension products of the one or more first primers. In some embodiments, the kit comprises a uracil DNA-glycosylase. In some embodiments, the kit comprises an endonuclease. In some embodiments, the kit comprises a polymerase. In some embodiments, the kit comprises a ligase. In some embodiments, the kit comprises a blocking polynucleotide that hybridizes to a sequence variant via sequence complementarity, wherein the sequence variant is at least 90% identical and less than 100% identical to a single-stranded target polynucleotide.

In one aspect, the present disclosure provides a polynucleotide complex. In some embodiments, the polynucleotide complex comprises a first single-stranded polynucleotide, a second-single stranded polynucleotide, and a capture probe, wherein the capture probe hybridizes at a 5' end to the first single-stranded polynucleotide and hybridizes at a 3' end to the second single-stranded polynucleotide, wherein the first single-stranded polynucleotide and the second single-stranded polynucleotide are non-contiguous, and wherein the capture probe comprises at least 10 deoxyuridines. In some embodiments, the first single-stranded polynucleotide comprises from a 5' end to a 3' end a first, a second, and a third segment wherein the first and second segments do not specifically hybridize to the capture probe via sequence complementarity and the third segment specifically hybridizes to the capture probe via sequence complementarity. In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality. In some embodiments, one of the first or second single-stranded polynucleotides is a cell-free polynucleotide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
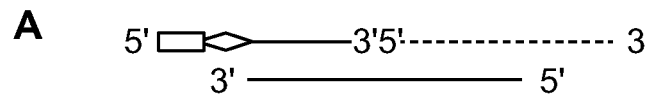
FIG. 1 illustrates complexes of polynucleotides that can be used to form ligation products, in accordance with some embodiments.
Figure 1:
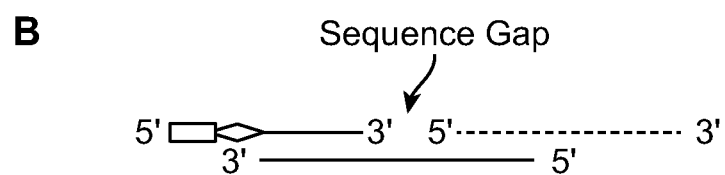
Figure 1:
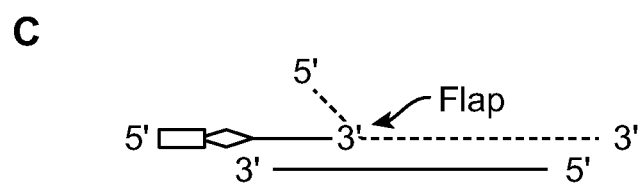

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide," "nucleic acid," and "oligonucleotide" are used interchangeably. As used herein, they generally refer to a polymeric form of nucleotides of any length, either deoxyribonucleotides or ribonucleotides, or analogs thereof. Polynucleotides may have any three dimensional structure, and may perform any function, known or unknown. Non-limiting examples of polynucleotides are coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adaptors, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target polynucleotide may be a portion of a larger polynucleotide (e.g. a portion to be amplified, sequenced, or otherwise analyzed), or may be used to refer to the larger polynucleotide comprising a target sequence. In general, the term "target sequence" refers to a nucleic acid sequence on a single strand of nucleic acid. The target sequence may be a portion of a gene, a regulatory sequence, genomic DNA, cDNA, fusion gene, RNA including mRNA, miRNA, rRNA, or others. The target sequence may be a target sequence from a sample or a secondary target such as a product of an amplification reaction.

The term "capture probe," as used herein, refers to a polynucleotide that interacts with one or more target polynucleotides, for example by hybridization. A capture probe can hybridize, partially or completely, to one or more target polynucleotides and any proportion of the hybridized region can be complementary. Thus, a capture probe is hybridizable to one or more polynucleotides. A capture probe may comprise one or more modified nucleotides, such as methylated nucleotides and nucleotide analogs. A capture probe may be further modified, such as by conjugation with a labeling component, tag, reactive moiety, or binding partner.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner, optionally with default settings), the BLAST algorithm (see e.g. the BLAST alignment tool, optionally with default settings), or the Smith-Waterman algorithm (see e.g. the EMBOSS Water aligner, optionally with default settings). Optimal alignment may be assessed using any suitable parameters of a chosen algorithm, including default parameters. In some embodiments, a capture probe specifically hybridizes to a specified target sequence via complementarity between a pre-determined, non-random sequence of the capture probe and the target sequence.

The terms "ligate" and "ligation," as used herein, refer to any enzymatic or non-enzymatic process by which an inter-nucleotide linkage is formed between two polynucleotide ends, which ends optionally are adjacently hybridized to a template. For example, the ends of DNA fragments can be ligated by forming a phosphodiester bond between the 3'-hydroxyl of one DNA terminus with the 5'-phosphoryl of another. In some cases, the inter-nucleotide linkage can be formed between two polynucleotide fragments (intermolecular). In some cases, the inter-nucleotide linkage can be formed between two terminal ends (5' end and 3' end) of a single fragment (intramolecular). Terminal ends of RNA fragments can similarly be joined by the formation of a phosphodiester bond. Polynucleotides that can be ligated may either be single-stranded or double-stranded. Double-stranded nucleic acids can comprise staggered ends, overhangs, or sticky ends where there are unpaired nucleotides at the 3' or 5' end of the DNA or RNA molecule. Double-stranded nucleic acids can comprise blunt ends, where the end nucleotides are paired at the 3' or 5' end of the DNA or RNA molecule. Ligation can comprise use of an enzyme, such as a ligase enzyme.

The term "adaptor," as used herein, generally refers to a nucleic acid which can be attached to another polynucleotide. For example, an adaptor can refer to a single-stranded polynucleotide which can be attached to a single-stranded polynucleotide (e.g., a cell-free polynucleotide, fragment of a cell-free polynucleotide, genomic DNA, or fragment of genomic DNA). In some cases, an adaptor can refer to a double-stranded nucleic acid which can be attached to a double-stranded nucleic acid. An adaptor can be attached to either a 5' end or a 3' end of a polynucleotide. In some cases, an adaptor can be attached to both ends of a polynucleotide, that is, one adaptor to each end.

The term "ligation product", as used herein, generally refers to a product resulting from a ligation reaction. In some cases, ligation product can refer to a DNA polynucleotide resulting from the ligation of two DNA polynucleotides. In some cases, ligation product can refer to a circular DNA polynucleotide resulting from the ligation of two ends of a linear DNA polynucleotide. In some cases, ligation product can refer to a RNA polynucleotide resulting from the ligation of two RNA polynucleotides. In some cases, ligation product can refer to a circular RNA polynucleotide resulting from the ligation of two ends of a linear RNA polynucleotide. In some cases, ligation product can refer to the polynucleotide product resulting from the ligation of a DNA polynucleotide and an RNA polynucleotide.

The terms "amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. In some cases, the amplification is effected by means of PCR using a pair of primers. Amplified products can be subjected to subsequence analyses, including but not limited to melting curve analysis, nucleotide sequencing, single-strand conformation polymorphism assay, allele-specific oligonucleotide hybridization, Southern blot analysis, and restriction endonuclease digestion.

The terms "isolated" and "isolating," with reference to a polynucleotide or polynucleotide complex, including but not limited to ligation products and amplification products, generally refers to a preparation of the substance (e.g., polynucleotide, polynucleotide complex, ligation products and amplification products thereof) devoid of at least some of the other components that may also be present where the substance or a similar substance naturally occurs or is initially obtained from (e.g., a biological sample, a sample reaction volume, e.g., a ligation reaction volume, an amplification reaction volume etc). For example, an isolated substance may be prepared using a purification technique to enrich it from a source mixture. Enrichment can be measured on an absolute basis or in terms of a concentration, for example in terms of weight per volume of solution, molecules per volume of solution, or any other appropriate measure.

The term "support," as used herein, generally refers to a substance having a surface on which another species can be immobilized. Non-limiting examples of supports include a particle (e.g., a bead), a surface of a well, a surface of a vessel, a solid surface, a planar surface, a surface of an array, a porous surface (e.g., a micro-cavity of a porous surface), a resin (e.g., a resin in a column) and a fiber (e.g., a fiber in a membrane or support). Moreover, a support can comprise any suitable material with non-limiting examples that include a metal, a metal oxide, carbonaceous materials and polymeric species. A support having a selective binding agent immobilized thereto may be used to, for example, isolate or enrich a species such as polynucleotide or polynucleotide complex comprising a tag which specifically binds the binding agent.

In various aspects, the present disclosure provides methods, compositions, reaction mixtures, kits, and systems for producing ligation products using a capture probe. Ligation products of the present disclosure can be further processed and analyzed using nucleic acid analysis methods, for example, sequencing to identify a sequence variant. In some embodiments, the methods are useful for generating ligation products comprising polynucleotides, including but not limited to, cell-free DNA and genomic DNA. Various aspects of the disclosure provide ligation products useful for downstream analysis, including but not limited to sequencing analysis and sequence variant identification.

In an aspect, the present disclosure provides a method for forming a ligation product. In some embodiments, a method for forming a ligation product of a first singled-stranded polynucleotide and a second single-stranded polynucleotide using a capture probe comprises: (a) mixing the first single-stranded polynucleotide and the second single-stranded polynucleotide with the capture probe to form a complex of polynucleotides, wherein a first segment of the capture probe can specifically hybridize with the first single-stranded polynucleotide via sequence complementarity and a second segment of the capture probe can specifically hybridize with the second single-stranded polynucleotide via sequence complementarity; (b) ligating the first single-stranded polynucleotide to the second single-stranded polynucleotide, thereby forming the ligation product; and (c) degrading or selectively removing the capture probe. In some embodiments, at least one of the first and second single-stranded polynucleotides comprises a cell-fee polynucleotide, for example a cell-free DNA polynucleotide, or genomic DNA. In some embodiments, at least one of the first and second single-stranded polynucleotides comprises a single-stranded adaptor.

Forming a complex of polynucleotides, herein used interchangeably with the term "polynucleotide complex," comprising a first single-stranded polynucleotide, and a second single-stranded polynucleotide with a capture probe can depend on the length (in nucleotides) of the hybridized portion, the degree of sequence complementarity between the first and second single-stranded polynucleotides and the respective segments of the capture probe to which they are each hybridized, and the temperature at which the mixing is conducted. The length of the hybridized portion comprising the first single-stranded polynucleotide and capture probe can be any suitable length, such as at least 20 base pairs (e.g. at least 25, 30, 35, 50, 100, 150, 200, 250, 300, 350, 400, 450, or 500 base pairs or more than 500 base pairs) in length, any portion of which may be complementary. The length of the hybridized portion comprising the first single-stranded polynucleotide and capture probe can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned. The length of the hybridized portion comprising the second single-stranded polynucleotide and capture probe can be any suitable length, such as at least 20 base pairs (e.g. at least 20, 25, 30, 35, 50, 100, 150, 200, 250, 300, 350, 400, 450, or 500 base pairs or more than 500 base pairs) in length, any portion of which may be complementary. The length of the hybridized portion comprising the second single-stranded polynucleotide and capture probe can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned. The formation of a complex of polynucleotides can also depend on the temperature of the mixture relative to the melting temperature of the hybridized regions. Melting temperature, also referred to as Tm, generally represents the temperature at which 50% of an oligonucleotide consisting of a reference sequence (which may in fact be a sub-sequence within a larger polynucleotide) and its complementary sequence are hybridized (or separated). Tm may be based on a standard calculation, algorithm, or measurement, available in the art. An example tool for measuring Tm, OligoAnalyzer, is made available by Integrated DNA Technologies, which may be set to use default parameters. Other similar tools are available. In some embodiments, a polynucleotide complex forms when the temperature of the mixture is within +15° C. of the Tm of the hybridized region comprising the first single-stranded polynucleotide and the capture probe or within +15° C. of the Tm of the hybridized region comprising the second single-stranded polynucleotide and the capture probe. In some embodiments, formation for a complex of polynucleotides is affected by other mixture conditions, including but not limited to buffer components and concentrations.

In some embodiments, the capture probe comprises a double-stranded nucleic acid and prior to forming a polynucleotide complex, the double-stranded nucleic acid is separated into two single-stranded capture probes. A double-stranded nucleic acid can be separated, for example, by heat denaturation or melting. In some embodiments, the first single-stranded polynucleotide and the second single-stranded polynucleotide are adjacent to each other when hybridized to the capture probe. This can occur, for example, in an arrangement where the first single-stranded polynucleotide is hybridized at the 3' end of the capture probe and the second single-stranded polynucleotide is hybridized at the 5' end of the capture probe, and the 3' end of the first single-stranded polynucleotide comprising a 3' terminal nucleotide is immediately adjacent to the 5' end of the second single-stranded polynucleotide comprising a 5' terminal nucleotide. In some embodiments, there is a sequence gap between the first single-stranded polynucleotide and the second single-stranded polynucleotide when each is hybridized to the capture probe. This can occur, for example, in an arrangement where the first single-stranded polynucleotide is hybridized at the 3' end of the capture probe and the second single-stranded polynucleotide is hybridized at the 5' end of the capture probe, and the 3' end of the first single-stranded polynucleotide comprising a 3' terminal nucleotide is not immediately adjacent to (e.g. separated by a gap of 1, 2, 3, 4, 5, 10, or more bases) the 5' end of the second single-stranded polynucleotide comprising a 5' terminal nucleotide. In some embodiments, the first single-stranded polynucleotide is extended to fill in a sequence gap between the first single-stranded polynucleotide and the second single-stranded polynucleotide using the capture probe as a template prior to or concurrent with ligation, as in step (b). Where filling in a gap is desired, a single-stranded polynucleotide (e.g. the first single-stranded polynucleotide) can be extended by an enzyme (e.g. a DNA polymerase, reverse transcriptase, or RNA polymerase) using the capture probe as a template in an extension reaction. A variety of polymerase enzymes useful in the subject methods are available, non-limiting examples of which are provided herein. In some embodiments, the second single-stranded polynucleotide comprises at a 5' end a segment lacking sequence complementarity to the capture probe. For example, in an arrangement where the first single-stranded polynucleotide is hybridized at the 3' end of the capture probe and the second single-stranded polynucleotide is hybridized at the 5' end of the capture probe, the segment at the 5' end of the second single-stranded polynucleotide lacking sequence complementarity to the capture probe may not hybridize and form a structure referred to as a "flap." Where desired, the flap can be removed. In some embodiments, the flap is cleaved prior to or concurrent with ligation, as in step (b). In some embodiments, the flap is cleaved by an endonuclease, such as a flap endonuclease. A variety of endonuclease enzymes useful in the subject methods are available, non-limiting examples of which are provided herein.

Illustrative embodiments of complexes of polynucleotides are shown in FIG. 1. A complex of polynucleotides wherein a first single-stranded polynucleotide and a second single-stranded polynucleotide are adjacent to each other when hybridized to a capture probe is shown in panel (A) of FIG. 1. A complex of polynucleotides wherein a sequence gap exists between a first single-stranded polynucleotide and a second single-stranded polynucleotide hybridized to a capture probe is shown in panel (B) of FIG. 1. A complex of polynucleotides wherein a second single-stranded polynucleotide comprises at a 5' end a segment lacking sequence complementarity to the capture probe, or a flap, is shown in panel (C) of FIG. 1.

In some embodiments, a ligation product is formed by ligating a first single-stranded polynucleotide to a second single-stranded polynucleotide when the first and second single-stranded polynucleotides are hybridized to a capture probe in a complex of polynucleotides. Where a first single-stranded polynucleotide and second single-stranded polynucleotide are adjacent to each other in a complex of polynucleotides, a ligation product can be formed by ligating a terminal nucleotide of the first single-stranded polynucleotide to a terminal nucleotide the second single-stranded polynucleotide. In some embodiments, a first single-stranded polynucleotide and a second single-stranded polynucleotide are ligated to form a ligation product concurrent with or following extension of the first single-stranded polynucleotide to fill a sequence gap. In some embodiments, a first single-stranded polynucleotide and a second single-stranded polynucleotide are ligated to form a ligation product concurrent with or following cleavage of a flap comprising a segment of the second single-stranded polynucleotide lacking sequence complementarity to the capture probe. Ligating the first single-stranded polynucleotide to the second single-stranded polynucleotide can comprise use of an enzyme, such as a ligase enzyme. A variety of ligase enzymes useful in the subject methods are available, non-limiting examples of which are provided herein. In some embodiments, a reaction mixture comprises reagents for two or more of, or all of, extension, flap cleavage, and ligation. In some embodiments, one or both of extension and flap cleavage are performed prior to ligation, any or all of which may be performed in separate reactions. The combination of flap cleavage and extension can be particularly advantageous when ligating a first polynucleotide to a particular location along a second polynucleotide, wherein the terminal sequence of the second polynucleotide is not known (such as in naturally occurring random fragments, and polynucleotides that are actively subjected to random fragmentation). In some embodiments, the terminal ends of the second polynucleotide are not formed by an endonuclease that leaves terminal ends having a known sequence. In some embodiments, the terminal ends of the second polynucleotide are formed by an endonuclease that leaves terminal ends having a known sequence.

In some embodiments, the capture probe is degraded or selectively removed concurrently with or after formation of a ligation product. Preferably, degradation or removal occurs after ligation. In some embodiments, degrading the capture probe comprises degrading the capture probe enzymatically or chemically. In some embodiments, the degradation is effected by an endonuclease (e.g. DNA endonuclease, RNA endonuclease). In some embodiments, a first single-stranded polynucleotide and a second single-stranded polynucleotide comprise DNA while the capture probe comprises RNA. In such cases, an RNA endonuclease that cleaves RNA (such as RNase H, which cleaves RNA in an RNA-DNA duplex) can be used to selectively degrade the RNA capture probe and not the first and second single-stranded DNA polynucleotides. In some embodiments, a first single-stranded polynucleotide and a second single-stranded polynucleotide comprise RNA while the capture probe comprises DNA. Use of a DNA endonuclease that cleaves DNA can selectively degrade the DNA capture probe and not the first and second single-stranded RNA polynucleotides. In some embodiments, a capture probe comprises one or more deoxyuridines, and the capture probe is degraded by a uracil DNA-glycosylase. A variety of endonuclease enzymes useful in the subject methods are available, non-limiting examples of which are provided herein. In some embodiments, the capture probe comprises a tag, and the capture probe is selectively removed with a binding element that selectively binds the tag. In some embodiments, the tag is biotin. Where selectively removing the capture probe comprising a biotin tag is desired, a binding element comprising avidin or modified avidin can be used.

In some embodiments, a complex of polynucleotides is isolated from the sample volume prior to degradation or selective removal of the capture probe. The complex of polynucleotides can be isolated to yield a sample preparation substantially free of reagents such as, but not limited to, unhybridized polynucleotides including first and second single-stranded polynucleotides; enzymes such as ligase and nucleases, e.g., endonucleases including flap endonucleases; and reagents including salts and other ions. By "substantially free" is meant that at least 50% (e.g., at least 60%, 70%, 80%, 90% or greater) of the starting amount is removed or not present in the sample preparation. A complex of polynucleotides can be isolated from a sample volume by immobilizing it directly or indirectly to a support comprising a selective binding agent that specifically binds a tag attached to the capture probe. A support may comprise a particle, a surface of a well, a surface of a vessel, a solid surface, a planar surface, a surface of an array, a porous surface (e.g., a micro-cavity of a porous surface), a resin (e.g., a resin in a column) and a fiber (e.g., a fiber in a membrane or support). In some embodiments, the support is a particle such as a bead, for example a magnetic bead. In some embodiments, the support is a resin such as a resin loaded into a purification column. Supports for isolating a complex of polynucleotides may have immobilized onto it a selective binding agent which can specifically interact with a tag, such as a tag attached to a capture probe. For example, polynucleotide complexes can be isolated from the sample reaction volume by selectively binding a tag attached to a capture probe of a polynucleotide complex to a selective binding agent, e.g., a binding agent immobilized to a support, and using the support to then remove the polynucleotide complexes from the sample solution. In this way, the polynucleotide complexes can be isolated from unligated polynucleotides prior to additional sample preparation steps.

The first single-stranded polynucleotide can comprise, from a 5' end to a 3' end, a first segment, a second segment, and a third segment wherein the first and second segments do not specifically hybridize to the capture probe via sequence complementarity and the third segment specifically hybridizes to the capture probe via sequence complementarity. In general, a first segment and a second segment that do not specifically hybridize to the capture probe are designed to not hybridize to the capture probe under conditions in which the third segment does hybridize to the capture probe. In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality.

The first segment of the first single-stranded polynucleotide comprising a sequence common to a plurality of different first single-stranded polynucleotides can be used in downstream processing of ligation products, including but not limited to amplification reactions and sequencing reactions for sequence analysis. For example, a sequence common to a plurality of different first single-stranded polynucleotides can comprise one or more amplification primer annealing sequences or complements thereof to amplify a plurality of ligation products. A sequence common to a plurality of different first single-stranded polynucleotides can comprise a probe binding site or a sequencing adaptor. A sequencing adaptor generally refers to oligonucleotides incorporated at the 5' and/or 3' ends of polynucleotides to facilitate one or more steps of a polynucleotide sequencing reaction. In some embodiments, a sequencing adaptor is used to bind a polynucleotide comprising the sequencing adaptor to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adaptors for flow cell attachment may comprise any suitable sequence compatible with next generation sequencing systems, e.g. 454 Sequencing, Ion Torrent Proton or PGM, and Illumina X10. Non-limiting examples of sequencing adaptors for next generation sequencing methods include P5 and P7 adaptors suitable for use with Illumina sequencing systems; TruSeq Universal Adapter; and TruSeq Indexed Adapter. In some embodiments, a sequencing adaptor is used to enrich for polynucleotides comprising the adaptor sequence, such as via amplification (e.g. by polymerase chain reaction (PCR)). A sequencing adaptor may also comprise a barcode and/or sample index sequence. A sequence common to a plurality of different first single-stranded polynucleotides can also comprise one or more sequencing primer annealing sequences or complements thereof; one or more restriction enzyme recognition sites; one or more random or near-random sequences; and combinations thereof. The first sequence can be of any suitable length. In some embodiments, the first sequence is at least 5, 10, 15, 20, 25, 30, 40, 50, or more nucleotides in length (e.g. between 5-30 or between 10-20 nucleotides in length).

The second segment of the first single-stranded polynucleotide comprising a barcode sequence that is not the same for all first single-stranded polynucleotides in the plurality can be used to distinguish a ligation product from a plurality of ligation products. A barcode sequence can refer to a known nucleic acid sequence that allows some feature of a polynucleotide with which the barcode is associated to be identified. Barcodes can each have a length within a range of 4 to 35 nucleotides, 6 to 30 nucleotides, or 8 to 20 nucleotides. In some embodiments, barcodes are at least 3, 4, 5, 6, 7, 8, 9, 10, 11, 12, 13, 14, or 15 nucleotides or more in length. In some embodiments, barcodes are less than 6 nucleotides in length. In some embodiments, barcodes associated with some target polynucleotides are a different length than barcodes associated with other target polynucleotides. The melting temperatures of barcodes within a set can be within +10° C. of one another, within +5° C. of one another, or within +2° C. of one another. Barcodes can be members of a minimally cross-hybridizing set. For example, the nucleotide sequence of each member of such a set can be sufficiently different from that of every other member of the set such that no member can form a stable duplex with the complement of any other member under moderate or stringent hybridization conditions. The nucleotide sequence of each member of a minimally cross-hybridizing set can differ from those of every other member by at least two nucleotides. In some embodiments, the barcode sequence of each first single-stranded polynucleotide in a single reaction is different from every other barcode sequence. In some embodiments, the barcode sequence is uniquely associated with a single ligation reaction in a plurality of ligation reactions.

In some embodiments, methods comprise amplifying the ligation product or a segment of the ligation product. Amplifying the ligation product or a segment of the ligation product can comprise using a first primer that specifically hybridizes to the first or the second segment of the first single-stranded polynucleotide, or a complement thereof, via sequence complementarity. Where sequencing analysis of the ligation product is desired, use of an amplification primer comprising a first sequencing adaptor can produce amplification products in which the nucleotide sequence of the first sequencing adaptor is appended to one end of the nucleotide sequence of a ligation product. The first sequencing adaptor can be used, for example, for binding by a sequencing primer or for attaching the amplification product to a flow cell for next generation sequencing. In some embodiments, the first primer comprises at a 5' end a first sequencing adaptor lacking sequence complementarity to the ligation product, or a complement thereof. A first primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides or more than 100 nucleotides, any portion or all of which may be complementary to the corresponding target sequence (e.g. about 5, 10, 15, 20, 25, 30, 35, 40, 45, or 50 nucleotides or more than 50 nucleotides). The length of a first primer for nucleic acid amplification can be within a range of 5 to 100 nucleotides, 10 to 85 nucleotides, 15 to 70 nucleotides, or 20 to 60 nucleotides, any portion or all of which may be complementary to the corresponding target sequence (e.g. about 5, 10, 15, 20, 25, 30, 35, 40, 45, or 50 nucleotides or more than 50 nucleotides). A first primer may comprise additional sequence elements including but not limited to a segment comprising one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adaptors (e.g. for attachment to a sequencing platform, such as a flow cell for massive parallel sequencing); one or more random or near-random sequences (e.g. one or more nucleotides selected at random from a set of two or more different nucleotides at one or more positions); and combinations thereof.

In some embodiments, the (i) first primer specifically hybridizes to the first segment of the first single-stranded polynucleotide, (ii) the first segment of the first single-stranded polynucleotide comprises a sequence common to a plurality of different first single-stranded polynucleotides, and (iii) the second segment of the first single-stranded polynucleotide comprises a barcode sequence that is not the same for all first single-stranded polynucleotides in the plurality.

In some embodiments, the ligation product or a segment of the ligation product is amplified using a second primer that specifically hybridizes to an extension product of the first primer via sequence complementarity. Where appending a second sequencing adaptor to a ligation product is desired, a second primer comprising a second sequencing adaptor can be used for amplification. The first and second sequencing adaptor may be the same or different. In some embodiments, the second primer comprises at a 5' end a second sequencing adaptor lacking sequence complementarity to an extension product of the first primer. Use of an amplification primer comprising a second sequencing adaptor can produce amplification products from extension products of the first primer in which the nucleotide sequence of an second sequencing adaptor is appended to one end of the sequence of a ligation product, for example at the 3' end of the ligation product if the sequencing adaptor of the first primer is appended at the 5' end of the ligation product. In some embodiments, the sequence of the additional sequencing adaptor is appended at the 5' end of the ligation product if the sequencing adaptor of the first primer is appended at the 3' end of the ligation product. In general, a 5' end refers to a portion of a polynucleotide that is 5' with respect to the 3' end, and optionally may include the 5'-terminal nucleotide. Similarly, a 3' end generally refers to a portion of a polynucleotide that is 3' with respect to the 5' end, and optionally may include the 3'-terminal polynucleotide. A second primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides, any portion or all of which may be complementary to the corresponding target sequence (e.g. about 5, 10, 15, 20, 25, 30, 35, 40, 45, or 50 nucleotides or more than 50 nucleotides). The length of a second primer for nucleic acid amplification can be within a range of 5 to 100 nucleotides, 10 to 85 nucleotides, 15 to 70 nucleotides, or 20 to 60 nucleotides, any portion or all of which may be complementary to the corresponding target sequence (e.g. about 5, 10, 15, 20, 25, 30, 35, 40, 45, or 50 nucleotides or more than 50 nucleotides).

In some embodiments, at least one of the first or second single-stranded polynucleotides is a cell-free polynucleotide, including but not limited to a cell-free DNA or RNA (cfDNA or cfRNA). The first and/or second single-stranded polynucleotides may be formed from double-stranded polynucleotides that are treated to render them single-stranded (e.g. by denaturation). In some embodiments, a cell-free polynucleotide is a circulating tumor DNA or RNA (ctDNA or ctRNA). In some embodiments, a cell-free polynucleotide comprises fetal DNA or RNA. In some embodiments, cell-free polynucleotides are polynucleotides originating from a cell but not directly obtained from a cellular source (e.g. by an extraction step comprising cell lysis). Non-limiting examples of sources from which cell-free polynucleotides may originate are normal cells and tissue, abnormal cells and tissue (e.g. cancerous cells or tissue), fetal cells and tissue, and pathogens. A cell-free polynucleotide present in a non-cellular source can result from cell death (e.g. apoptosis or necrosis) or cell shedding. Sequence analysis of cell-free polynucleotides can be used to characterize the cell or population of cells from which the cell-free DNA is derived, such as tumor cells (e.g. in cancer detection), fetal cells (e.g. in prenatal diagnostics), cells from transplanted tissue (e.g. in early detection of transplant failure), or a pathogen (e.g. bacteria or virus). In some embodiments, at least one of the first or second single-stranded polynucleotides is a fragment of genomic DNA. In some embodiments, at least one of the first or second single-stranded polynucleotides comprises a sequence or sequences resulting from a chromosomal rearrangement. In some embodiments, the chromosomal rearrangement is at least one of a deletion, duplication, inversion, and translocation.

Figure 2:
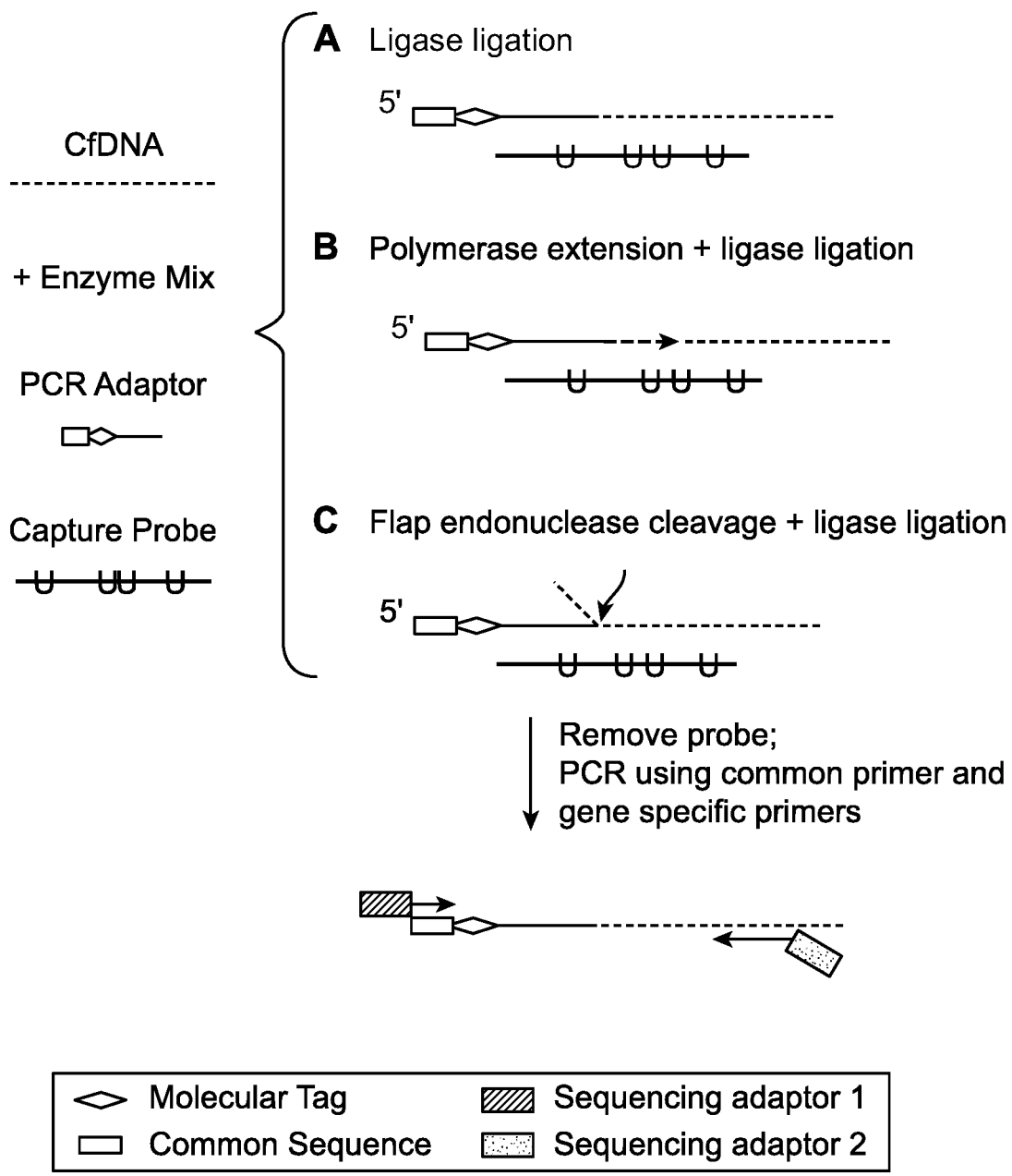
FIG. 2 illustrates a method for forming ligation products, in accordance with an embodiment.

An illustrative embodiment of a method of forming ligation products is shown in FIG. 2. A plurality of second single-stranded polynucleotides, for example cell-free DNAs (cfDNAs), can form complexes of polynucleotides further comprising a first single-stranded polynucleotide, for example a PCR adaptor, and a capture probe comprising deoxyuridines. The first single-stranded polynucleotide and the second single-stranded polynucleotide can be immediately adjacent to each other when hybridized to a capture probe as show in panel (A) of FIG. 2. A ligase can effect the formation of a ligation product. There can be a sequence gap between the first single-stranded polynucleotide and the second single-stranded polynucleotide hybridized to the capture probe. This sequence gap can be filled in with a polymerase as shown in panel (B) of FIG. 2 prior to or concurrent with ligation, which can be effected by a ligase. A segment of a second single-stranded polynucleotide lacking sequence complementarity to the capture probe can form a flap as shown in panel (C) of FIG. 2. A flap can be cleaved with a flap endonuclease prior to or concurrent with ligation, which can be effected by a ligase. The capture probes comprising deoxyuridines can be degraded with uracil DNA-glycosylase, and the ligation product can be amplified with first and second primers comprising sequencing adaptors.

In some embodiments, a ligation reaction comprises a plurality of single-stranded polynucleotides comprising a plurality of sequences for forming ligation products. Some samples may contain sequences that are high in sequence similarity, for example polynucleotides comprising a mutant sequence and a wild-type sequence that differ by at least one base. The high sequence similarity between a desired sequence, for example a mutant sequence, and an undesired sequence, for example a wild-type sequence, can result in hybridization of both polynucleotides to a capture probe and the formation of ligation products comprising the undesired sequence. In some embodiments, the undesired sequence variant is at least 90% identical (e.g. at least 95%, or 99% identical) and less than 100% identical to the desired sequence. In some embodiments, an additional polynucleotide is added to a reaction to prevent or decrease hybridization between the capture probe and the undesired sequence variant, for example a wild-type sequence. In some embodiments, mixing the first single-stranded polynucleotide, the second single-stranded polynucleotide, and the capture probe to form a complex of polynucleotides comprises use of a blocking polynucleotide that hybridizes to a sequence variant via sequence complementarity, wherein the sequence variant is at least 90% identical and less than 100% identical to the second single-stranded polynucleotide.

Figure 3:
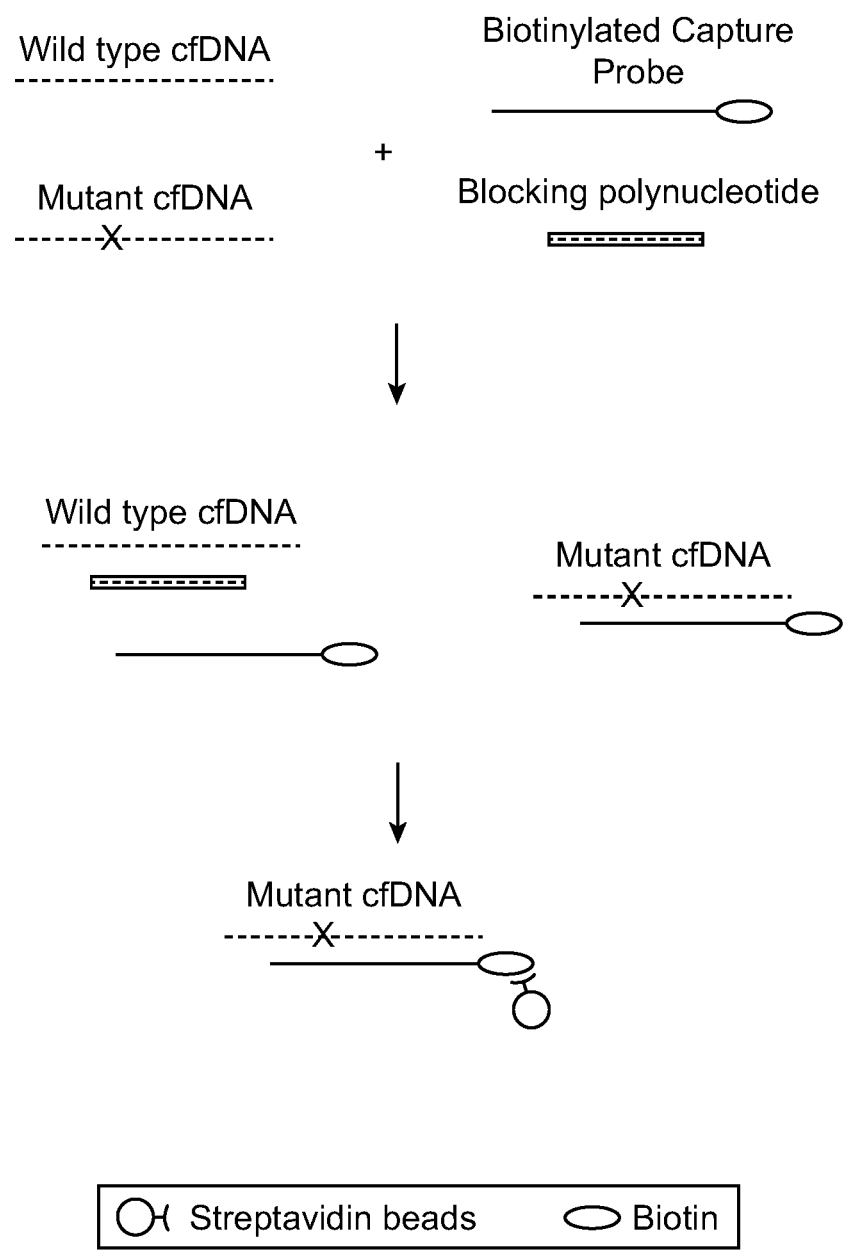
FIG. 3 illustrates a use of a blocking polynucleotide, in accordance with an embodiment.

An illustrative embodiment of a method of using a blocking polynucleotide is shown in FIG. 3. A mixture of polynucleotides comprising wild type (wt) and mutant cfDNA are mixed with capture probes comprising biotin tags and blocking polynucleotides that can hybridize to wt cfDNA via sequence complementarity. The mutant cfDNA can hybridize to a capture probe whereas a blocking polynucleotide hybridized to wt cfDNA can prevent the wt cfDNA from hybridizing to the capture probe. A binding element comprising streptavidin beads can be used to remove the capture probe hybridized to the mutant cfDNA.

In some embodiments, the blocking polynucleotide is 100% complementary to the sequence variant. In some embodiments, the blocking polynucleotide does not block all sequence variants from hybridizing to a capture probe, but does enrich capture of a target sequence relative to a proportion captured in the absence of the blocking polynucleotide. In some embodiments, use of a blocking polynucleotide results in ligation products wherein about 90% comprise the first single-stranded polynucleotide and about 10% comprise the sequence variant. In some embodiments, use of a blocking polynucleotide results in ligation products wherein about 80% comprise the first single-stranded polynucleotide and about 20% comprise the sequence variant. In some embodiments, use of a blocking polynucleotide results in ligation products wherein between 60% and 100% of the ligation products comprise the first single-stranded polynucleotide and between 40% and 0% of the ligation products comprise the sequence variant. The sequence and length of a blocking polynucleotide can be designed such that its melting temperature is more sensitive to mismatched bases than a capture probe, allowing the blocking polynucleotide to bind preferentially to its target sequence (e.g. the sequence variant). A blocking polynucleotide can comprise modified bases to further increase the Tm difference of perfectly matched versus mismatched targets. A blocking polynucleotide can be of any suitable length. In some embodiments, a blocking polynucleotide is at least 5 nucleotides (e.g. 6, 7, 8, 9, 10, 15, 20, 25, 30, 40, 50, 60, 70, 80, or 100 nucleotides or more than 100 nucleotides) in length. The length of a blocking polynucleotide can be within a range of 5 to 100 nucleotides, 10 to 85 nucleotides, 15 to 70 nucleotides, or 20 to 60 nucleotides. A blocking polynucleotide can comprise nucleotides such as LNAs (locked nucleic acids), deoxyribonucleotides and ribonucleotides. In some embodiments, a blocking polynucleotide comprises at least 1 modified nucleotide (e.g. at least 2, 3, 4, 5, 6, 7, 8, 9, 10, 15, 20, 25, 30, 40, or 50 modified nucleotides or more than 50 modified nucleotides). In some embodiments, the blocking polynucleotide comprises at least 1% modified nucleotides (e.g. at least 2%, 3%, 4%, 5%, 6%, 7%, 8%, 9%, 10%, 25%, 20%, 30%, 40%, 50%, 60%, 70%, or 80% modified nucleotides or more than 80% modified nucleotides). The blocking polynucleotide may comprise deoxyuridines. In some embodiments, the blocking polynucleotide comprises at least 1 deoxyuridine (e.g. at least 2, 3, 4, 5, 6, 7, 8, 9, 10, 20, or 30 deoxyuridines or more than 30 deoxyuridines). In some embodiments, the blocking polynucleotide comprises at least 1% deoxyuridines (e.g. at least 2%, 3%, 4%, 5%, 6%, 7%, 8%, 9% or 10% deoxyuridines or more than 10% deoxyuridines). A blocking polynucleotide can be further modified, such as with a tag, examples of which are described elsewhere herein. In some embodiments, the blocking polynucleotide is degraded. Degrading a blocking polynucleotide can comprise enzymatic or chemical degradation. In some embodiments, the blocking polynucleotide comprises a tag useful for the selective removal of the capture probe. In some embodiments, the tag comprises a biotin tag that can bind a binding element comprising an avidin, modified avidin, or streptavidin protein. In some embodiments, the tag comprises a digoxigenin tag that can bind a binding element comprising an anti-digoxigenin antibody. In some embodiments, the tag comprises a dinitrophenol (DNP) tag that can bind a binding element comprising an anti-DNP antibody.

In some embodiments, the tag comprises a fluorescein tag that can bind a binding element comprising an anti-fluorescein antibody.

Figure 4:
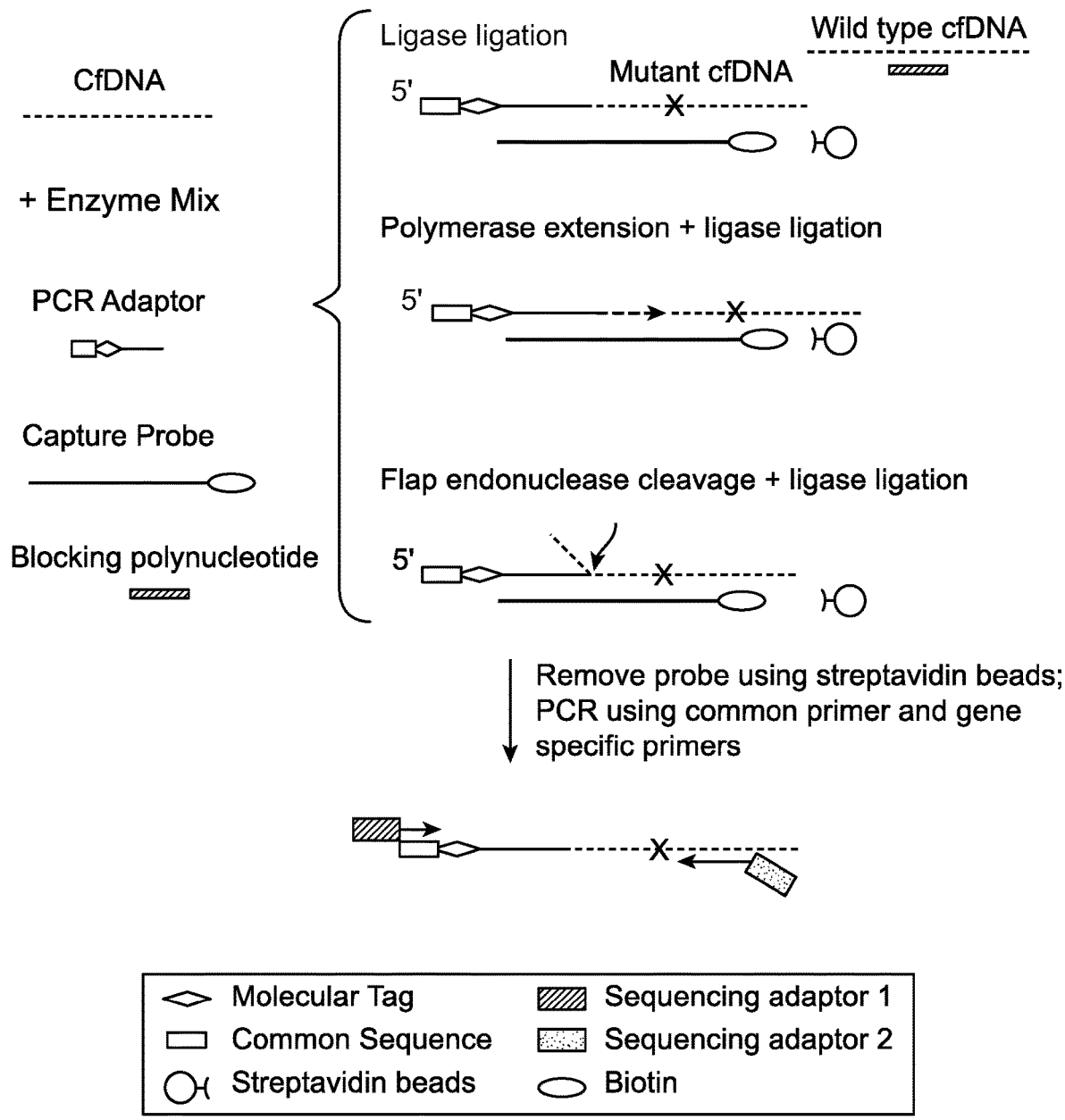
FIG. 4 illustrates a method for forming ligation products, in accordance with an embodiment.
Figure 5:
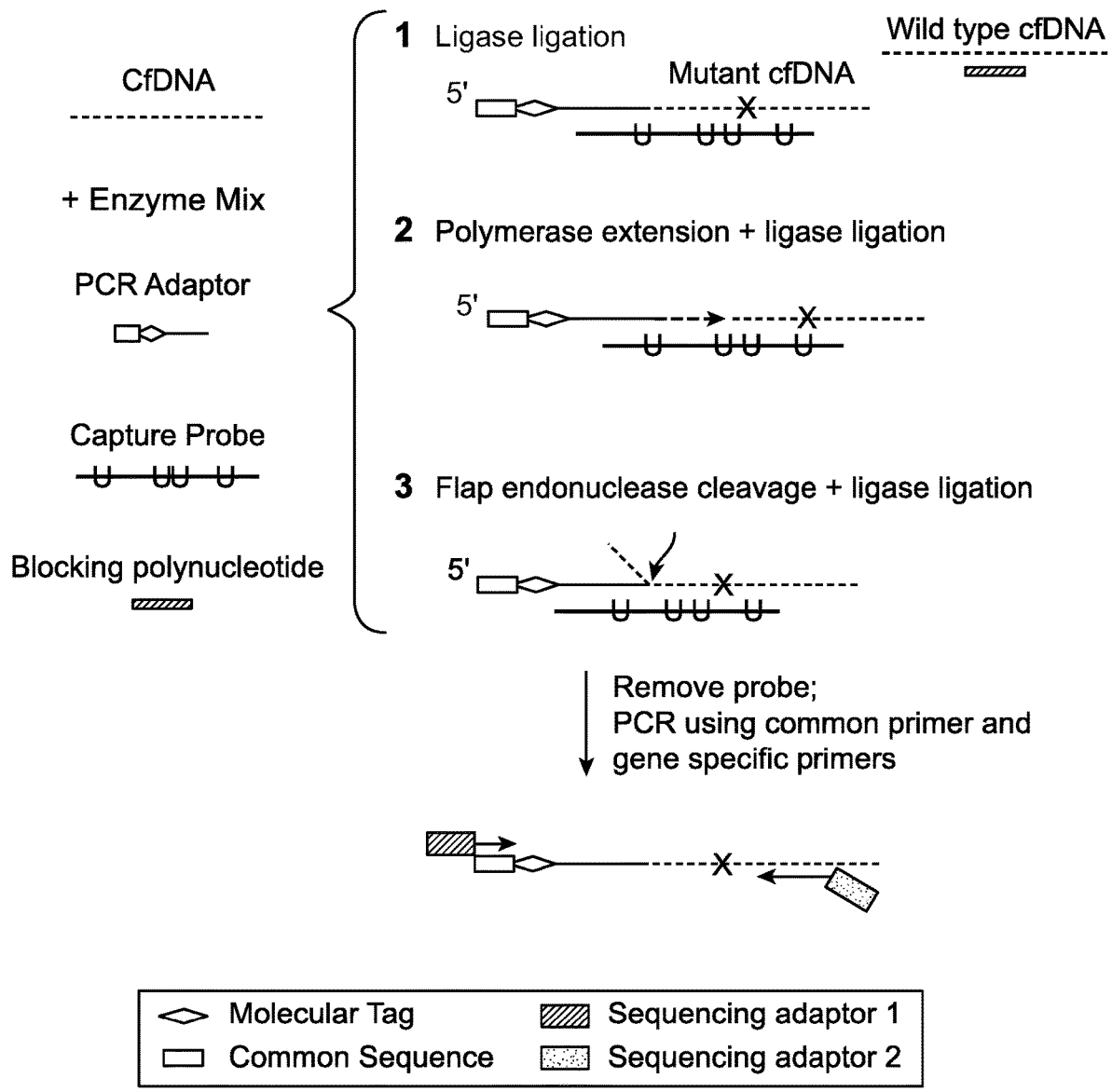
FIG. 5 illustrates a method for forming ligation products, in accordance with an embodiment.

An illustrative embodiment of a method of forming ligation products using a blocking polynucleotide is shown in FIG. 4. Mixtures of first single-stranded polynucleotides comprising PCR adaptors, second single-stranded polynucleotides comprising cfDNA, capture probes comprising biotin tags, and blocking polynucleotides designed to bind to wt cfDNA can form complexes of polynucleotides comprising mutant cfDNA, PCR adaptors and capture probes. The presence of blocking polynucleotides designed to bind to wt cfDNA can decrease the number of complexes of polynucleotides comprising wt cfDNA, either partially or completely. Ligases can effect the formation of ligation products comprising mutant cfDNA and PCR adaptors. Where a sequence gap exists between the mutant cfDNA and PCR adaptor hybridized to a capture probe, a polymerase can extend the PCR adaptor to fill a sequence gap prior to or concurrent with ligation. Where the mutant cfDNA comprises at a 5' end a segment lacking sequence complementarity to the capture probe, a flap endonuclease can cleave the segment lacking sequence complementarity prior to or concurrent with ligation. Capture probes can be removed using binding elements comprising streptavidin beads and the ligation product can be amplified using primers comprising sequencing adaptors, for example PCR primers comprising common sequences or gene specific sequences. In another illustrative embodiment, a capture probe comprises deoxyuridines as shown in FIG. 5 and can be removed by uracil DNA-glycosylase.

In an aspect, the present disclosure provides a method for amplifying a polynucleotide, such as a cell-free DNA, genomic DNA, or fragment thereof. In some embodiments, the method comprises: (a) forming a ligation product by ligating a cell-free DNA polynucleotide to a single-stranded adaptor polynucleotide of a polynucleotide complex, wherein the polynucleotide complex comprises a first segment of a capture probe hybridized to a cell-free DNA polynucleotide and a second segment of the capture probe hybridized to a single-stranded adaptor; (b) degrading or selectively removing the capture probe; (c) circularizing the ligation product to yield a circular target polynucleotide; (d) generating a concatemer comprising a single-stranded polynucleotide from the circular target polynucleotide by extension of a first primer that hybridizes to the target polynucleotide via sequence complementarity; and (e) generating a plurality of extension products containing one or more copies of the target polynucleotide by extension of a second primer that hybridizes to the concatemer via sequence complementarity.

Ligation products, as formed by methods of the present disclosure, can be circularized to yield circular target polynucleotides. Circularization can include joining the 5' end of a polynucleotide to the 3' end of the same polynucleotide, to the 3' end of another polynucleotide in a sample, or to the 3' end of a polynucleotide from a different source (e.g. an artificial polynucleotide, such as an oligonucleotide adaptor). In some embodiments, the 5' end of a polynucleotide is joined to the 3' end of the same polynucleotide (also referred to as "self-joining" or "intramolecular ligation"). In some embodiments, conditions of the circularization reaction are selected to favor self-joining of polynucleotides within a particular range of lengths, so as to produce a population of circularized polynucleotides of a particular average length. For example, circularization reaction conditions may be selected to favor self-joining of polynucleotides shorter than about 5000, 2500, 1000, 750, 500, 400, 300, 200, 150, 100, 50, or fewer nucleotides in length. In some embodiments, fragments having lengths between 50-5000 nucleotides, 100-2500 nucleotides, or 150-500 nucleotides are favored, such that the average length of circularized polynucleotides falls within the respective range. In some embodiments, 80% or more of the circularized fragments are between 50-500 nucleotides in length, such as between 50-200 nucleotides in length. Reaction conditions that may be optimized include the length of time allotted for a joining reaction, the concentration of various reagents, and the concentration of polynucleotides to be joined. In some embodiments, a circularization reaction preserves the distribution of fragment lengths present in a sample prior to circularization. For example, one or more of the mean, median, mode, and standard deviation of fragment lengths in a sample before circularization and of circularized polynucleotides are within 75%, 80%, 85%, 90%, 95%, or more of one another.

Circularized ligation products disclosed herein can comprise a 5' end of a cell-free DNA polynucleotide joined to a 3' end of a single-stranded adaptor and a 3' end of the cell-free DNA polynucleotide joined to a 5' end of the single-stranded adaptor. An adaptor includes any oligonucleotide having a sequence, at least a portion of which is known, that can be joined to a sample polynucleotide. Adaptor oligonucleotides can comprise DNA, RNA, nucleotide analogues, non-canonical nucleotides, labeled nucleotides, modified nucleotides, or combinations thereof. Adaptor oligonucleotides can be single-stranded, double-stranded, or partial duplex. In general, a partial-duplex adaptor comprises one or more single-stranded regions and one or more double-stranded regions. Double-stranded adaptors can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, identical adaptors are added to both ends of a target polynucleotide. For example, first and second adaptors can be added to the same reaction.

An adaptor can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adaptors or subsets of different adaptors, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adaptors comprising the random sequence), and combinations thereof. In some cases, the adaptors may be used to purify those circles that contain the adaptors, for example by using beads (particularly magnetic beads for ease of handling) that are coated with oligonucleotides comprising a complementary sequence to the adaptor, that can "capture" the closed circles with the correct adaptors by hybridization thereto, wash away those circles that do not contain the adaptors and any unligated components, and then release the captured circles from the beads. In addition, in some cases, the complex of the hybridized capture probe and the target circle can be directly used to generate concatamers, such as by direct rolling circle amplification (RCA). In some embodiments, the adaptors in the circles can also be used as a sequencing primer. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adaptor. A sequence element may be of any suitable length, such as about or less than about 3, 4, 5, 6, 7, 8, 9, 10, 15, 20, 25, 30, 35, 40, 45, 50 or more nucleotides in length. Adaptor oligonucleotides can have any suitable length, at least sufficient to accommodate the one or more sequence elements of which they are comprised. In some embodiments, adaptors are about or less than about 10, 15, 20, 25, 30, 35, 40, 45, 50, 55, 60, 65, 70, 75, 80, 90, 100, 200, or more nucleotides in length. In some embodiments, an adaptor oligonucleotide is in the range of about 12 to 40 nucleotides in length, such as about 15 to 35 nucleotides in length.

In some embodiments, the adaptor oligonucleotides joined to a single-stranded polynucleotide (e.g., cell-free DNA polynucleotide, genomic DNA, or fragment thereof) from one sample comprise one or more sequences common to all adaptor oligonucleotides and a barcode that is unique to the adaptors joined to polynucleotides of that particular sample, such that the barcode sequence can be used to distinguish polynucleotides originating from one sample or adaptor joining reaction from polynucleotides originating from another sample or adaptor joining reaction. In some embodiments, an adaptor oligonucleotide comprises a 5' overhang, a 3' overhang, or both that is complementary to one or more target poly nucleotide overhangs. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs of an adaptor oligonucleotide may comprise a random sequence of one or more nucleotides, such that one or more nucleotides are selected at random from a set of two or more different nucleotides at one or more positions, with each of the different nucleotides selected at one or more positions represented in a pool of adaptors with complementary overhangs comprising the random sequence. In some embodiments, an adaptor overhang is complementary to a target polynucleotide overhang produced by restriction endonuclease digestion. In some embodiments, an adaptor overhang consists of an adenine or a thymine.

A variety of methods for circularizing polynucleotides are available. In some embodiments, circularization comprises an enzymatic reaction, such as use of a ligase (e.g. an RNA or DNA ligase). A variety of ligases are available, including, but not limited to, CircLigase™ (Epicentre; Madison, WI), RNA ligase, T4 RNA Ligase 1 (ssRNA Ligase, which works on both DNA and RNA). In addition, T4 DNA ligase can also ligate ssDNA if no dsDNA templates are present, although this is generally a slow reaction. Other non-limiting examples of ligases include NAD-dependent ligases including Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Where self-joining is desired, the concentration of polynucleotides and enzyme can be adjusted to facilitate the formation of intramolecular circles rather than intermolecular structures. Reaction temperatures and times can be adjusted as well. In some embodiments, 60° C. is used to facilitate intramolecular circles. In some embodiments, reaction times are between 12-16 hours. Reaction conditions may be those specified by the manufacturer of the selected enzyme. In some embodiments, an exonuclease step can be included to digest any unligated nucleic acids after the circularization reaction. That is, closed circles do not contain a free 5' or 3' end, and thus the introduction of a 5' or 3' exonuclease will not digest the closed circles but will digest the unligated components. This may find particular use in multiplex systems.

Circularization may be followed directly by sequencing the circularized polynucleotides. Alternatively, sequencing may be preceded by one or more amplification reactions. In some embodiments, the polynucleotide complexes, ligation products, or circularized polynucleotides are isolated or enriched prior to amplification. Isolation can be achieved by various suitable purification methods including affinity purification. For example, polynucleotide complexes, ligation products, or circularized polynucleotides can be isolated by binding of a selective binding agent immobilized on a support to a tag attached to the capture probe. The support can then be used to separate or isolate the capture probe and any polynucleotide hybridized to the capture probe from the other contents of the sample reaction volume. The isolated polynucleotides can then be used for amplification and further sample preparation steps. In some embodiments, the capture probe is degraded or selectively removed prior to amplification of the circular target polynucleotides.

In general, "amplification" refers to a process by which one or more copies are made of a target polynucleotide or a portion thereof. A variety of methods of amplifying polynucleotides (e.g. DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. Nos. 5,527,670, 6,033,850, 5,939,291, and 6,333,157), and application of an electromagnetic field in combination with primers bound to a magnetically-responsive material (e.g. U.S. Pat. No. 5,545,540).

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. Nos. 5,270,184 and 5,455,166). Thermophilic SDA (tSDA) uses thermophilic endonucleases and polymerases at higher temperatures in essentially the same method (European Pat. No. 0 684 315). Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278). In some cases, isothermal amplification utilizes transcription by an RNA polymerase from a promoter sequence, such as may be incorporated into an oligonucleotide primer. Transcription-based amplification methods include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) *BioTechnol.* 6, 1197-1202); self-sustained sequence replication (e.g., Guatelli, J. et al. (1990) *Proc. Natl. Acad. Sci. USA* 87, 1874-1878; Landgren (1993) *Trends in Genetics* 9, 199-202; and HELEN H. LEE et al., NUCLEIC ACID AMPLIFICATION TECHNOLOGIES: Application to Disease Diagnosis (1997) Birkhäuser); and methods for generating additional transcription templates (e.g. U.S. Pat. Nos. 5,480,784 and 5,399,491). Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. Nos. 6,251,639, 6,946,251, and 7,824,890). Isothermal amplification processes can be linear or exponential.

Rolling circle amplification can be used to generate a concatemer from a ligation product. A concatemer can be formed by extension of a first primer that hybridizes to a circular target polynucleotide via sequence complementarity and copies around the circular template at least one time around. A primer that copies at least two times around the circular template can contain at least two copies of the target polynucleotide. Similarly, a primer that copies at least three times around the circular template can contain at least three copies of the target polynucleotide. In general, a concatemer is a polynucleotide amplification product comprising at least one copy of a target sequence from a template polynucleotide (e.g. about or more than about 1, 2, 3, 4, 5, 6, 7, 8, 9, 10, or more copies of the target sequence; in some embodiments, about or more than about 2 copies).

A typical RCA reaction mixture comprises one or more primers, a polymerase, and dNTPs, and produces concatemers. Typically, the polymerase in an RCA reaction is a polymerase having strand displacement activity. A variety of such polymerases are available, non-limiting examples of which include exonuclease minus DNA Polymerase I large (Klenow) Fragment, Phi29 DNA polymerase, Taq DNA Polymerase, Bsu DNA polymerase, Vent polymerase, Bst polymerase, PyroPhage3173 polymerase, and the like.

A concatemer generated by extension of a first primer that hybridizes to the target polynculeotide can be used as a template for primer extension of a second primer. A second primer that hybridizes to the concatemer via sequence complementarity can be extended in a primer extension reaction to product an extension product containing one or more copies of the target polynucleotide. Where a concatemer contains at least one copy of the target polynucleotide sequence, a plurality of second primers can hybridize to various segments of the concatemer and yield a plurality of extension products via primer extension.

Amplification primers, e.g., a first primer and a second primer, may be of any suitable length, such as about or at least about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, or at least about 5, 10, 15, 20, 25, 30, 35, 40, 45, 50, or more nucleotides). In some embodiments, a first primer which is used to generate the concatemer hybridizes to a sequence of at least a segment of the cell-free DNA polynucleotide. The first primer can comprise, for example, a gene specific sequence and hybridize to ligation products comprising a target gene sequence which is desired to be analyzed. In some embodiments, the first primer comprises a random sequence. In general, a random primer comprises one or more random or near-random sequences (e.g. one or more nucleotides selected at random from a set of two or more different nucleotides at one or more positions, with each of the different nucleotides selected at one or more positions represented in a pool of adaptors comprising the random sequence). In this way, polynucleotides (e.g. all or substantially all circularized polynucleotides) can be amplified in a sequence non-specific fashion. In some embodiments, the first primer which is used to generate the concatemer hybridizes to a sequence of at least a segment of the single-stranded adaptor, for example a sequence of the single-stranded adaptor that is common to all single-stranded adaptors of a plurality of ligation products. In this way, concatemers can be generated from all ligation products using the same first primer sequence.

In some embodiments, the second primer which is used to generate extension products from a concatemer hybridizes to a sequence complementary to at least a segment of the cell-free DNA polynucleotide. The second primer can comprise, for example, a gene specific sequence and hybridize to concatemers comprising a target gene sequence (or complement thereof) which is desired to be analyzed. In some embodiments, the second primer comprises a random sequence. In some embodiments, the second primer which is used to generate extension products from a concatemer hybridizes to a sequence complementary to at least a segment of the single-stranded adaptor, for example a sequence of the single-stranded adaptor that is common to all single-stranded adaptors of a plurality of ligation products. In this way, extension products can be generated from all concatemers using the same second primer sequence.

In some embodiments, multiple target-specific primers for a plurality of targets are used in the same reaction. For example, target-specific primers for about or at least about 10, 50, 100, 150, 200, 250, 300, 400, 500, 1000, 2500, 5000, 10000, 15000, or more different target sequences may be used in a single amplification reaction in order to amplify a corresponding number of target sequences (if present) in parallel. Multiple target sequences may correspond to different portions of the same gene, different genes, or non-gene sequences. Where multiple primers target multiple target sequences in a single gene, primers may be spaced along the gene sequence (e.g. spaced apart by about or at least about 50 nucleotides, every 50-150 nucleotides, or every 50-100 nucleotides) in order to cover all or a specified portion of a target gene. In some embodiments, both primers having gene specific sequences and primers which hybridize to a common sequence of an adaptor are used for amplification.

In some embodiments, a primer for amplification comprises a 3' end which hybridizes to the target sequence via sequence complementarity and a 5' end that does not hybridize to the target sequence via sequence complementarity. For example, the first primer can comprise a first 3' end which hybridizes to a target polynucleotide via sequence complementarity and a first 5' end that does not hybridize to a target polynucleotide via sequence complementarity. For further example, the second primer can comprise a second 3' end which hybridizes to a concatemer via sequence complementarity and a second 5' end that does not hybridize to the concatemer via sequence complementarity. A 5' end of a primer that does not hybridize to a target sequence (e.g., a target polynucleotide or concatemer) via sequence complementarity may comprise sequence elements including, but not limited to, one or more amplification primer annealing sequences or complements thereof, one or more sequencing primer annealing sequences or complements thereof, one or more barcode sequences, one or more common sequences shared among multiple different primers, one or more restriction enzyme recognition sites, one or more probe binding sites or sequencing adaptors (e.g., for attachment to a sequencing platform, such as a flow cell for massive parallel sequencing), one or more random or near-random sequences, and combinations thereof. In some embodiments, the 5' ends of the first and second primers comprise one or more amplification primer annealing sequences or complements thereof and the method further comprises amplifying the plurality of extension products using a third primer comprising a sequence of at least a portion of the first 5' end and a fourth primer comprising a sequence of at least a portion of the second 5' end.

In some embodiments, amplification comprises multiple cycles of rolling circle amplification (RCA). An amplification reaction mixture can be subjected to multiple cycles of rolling circle amplification to generate a plurality of amplification products comprising concatemers. The amplification reaction mixture can comprise (i) a polymerase having strand displacement activity, (ii) a circular target polynucleotide generated according to methods disclosed herein, and (iii) primers. Each cycle of the multiple cycles of rolling circle amplification can comprise denaturation at a denaturing temperature, primer annealing at an annealing temperature, and primer elongation at an elongation temperature for a give elongation time period. The plurality of amplification products generated can be characterized in that it contains a higher proportion of concatemers having at least two copies of the target polynucleotide as compared to a plurality of amplification products generated by utilizing one cycle of amplification under comparable conditions for denaturation and primer annealing but with an elongation time period comparable to a sum of the elongation time period of the multiple cycles. Multiple cycles of RCA can result in the formation of a plurality of linear concatemers from a circular template. During denaturation, extension of a first concatemer from a circular template is terminated. By repeating primer binding and extension, a plurality of concatemers can be generated from a circular template over multiple cycles. In some embodiments, three temperature phases are used—a first temperature phase for denaturation, a second temperature phase for primer binding, and a third temperature phase for primer extension. In some embodiments, a temperature for primer extension that is higher than for primer binding is selected to minimize primer binding during primer extension. Minimizing primer binding during primer extension can decrease the formation of shorter amplification products and reduce biased amplification of short fragments, as primers are less likely to hybridize to amplification products as they are being formed, such as in the case of a reverse primer included in the amplification reaction mixture. Primers hybridized to amplification products as they are being formed can also participate in primer extension but may result in preferential amplification of small fragments, as during extension, small circles tend to generate more copies of repeated units and more primer binding sites than large fragments within a given period of time.

Figure 6A:
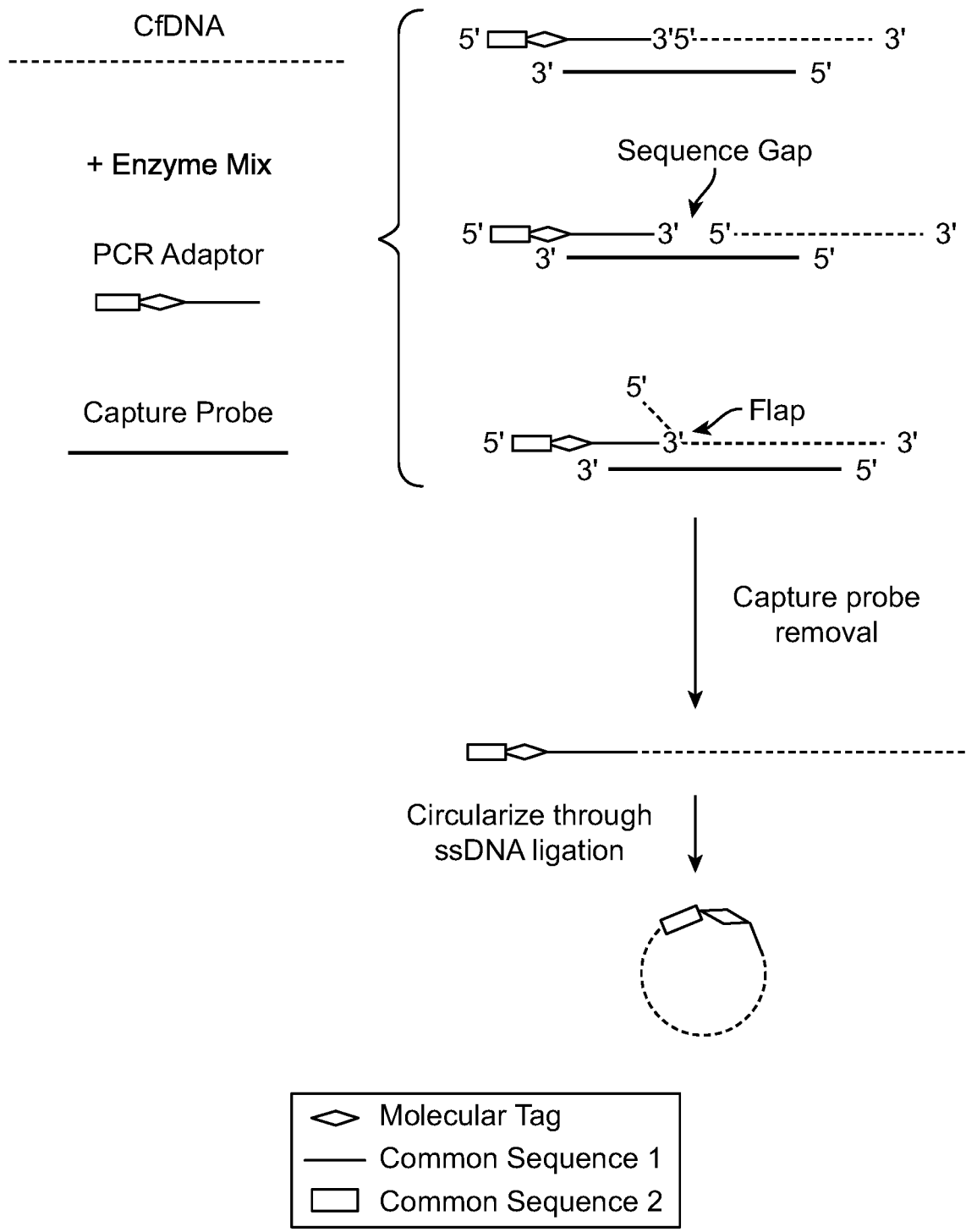
FIGS. 6A and 6B illustrate a method for amplifying a polynucleotide, in accordance with an embodiment.
Figure 6B:
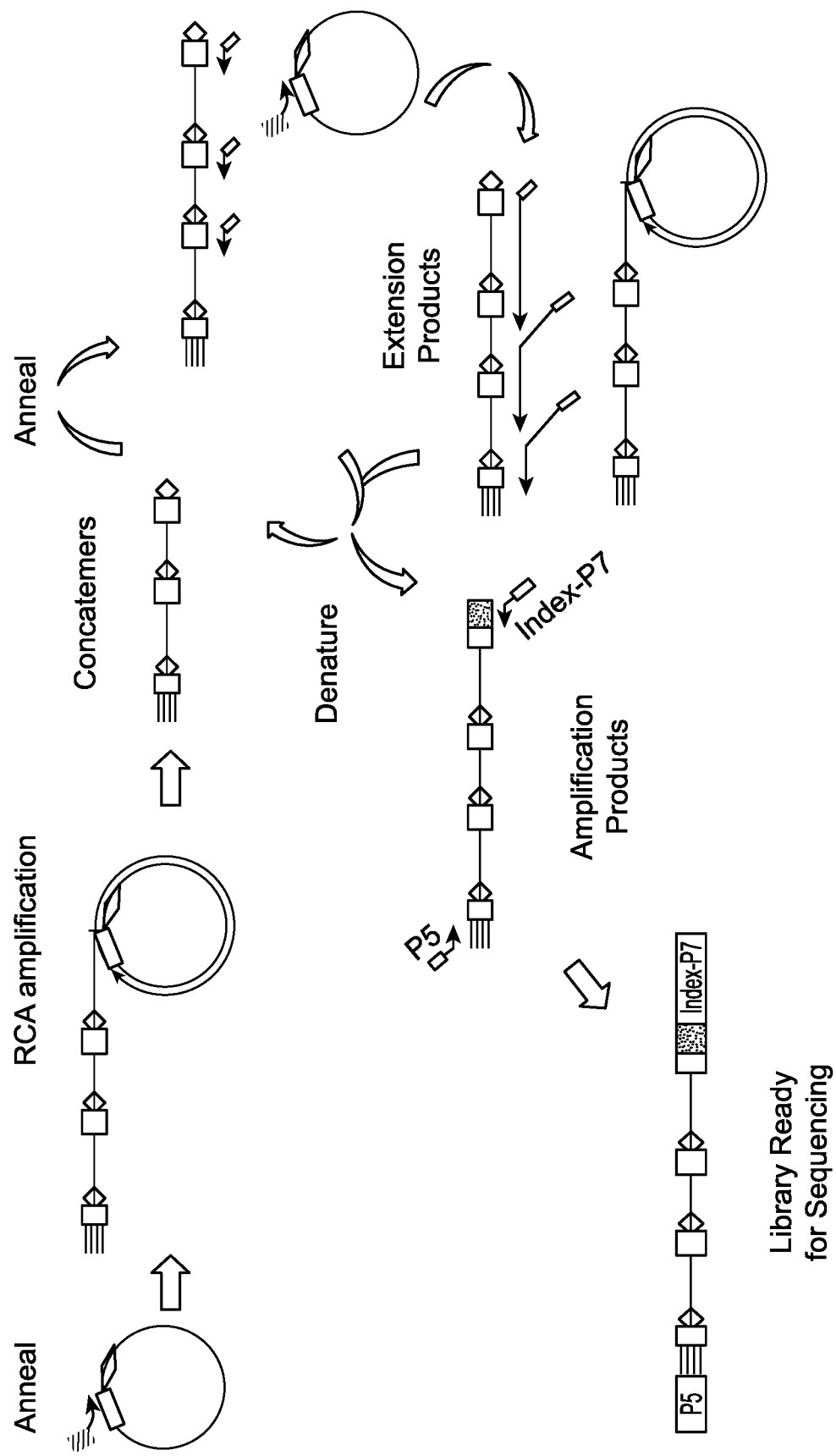

An illustrative embodiment of a method of amplifying a polynucleotide is shown in FIGS. 6A and 6B. As shown in FIG. 6A, a cell-free DNA polynucleotide, single-stranded adaptor, and capture probe can form a polynucleotide complex. In some cases, the cell-free DNA polynucleotide and the single-stranded adaptor can be immediately adjacent to each other when hybridized to a capture probe and ligase can effect the formation of a ligation product. In some cases, there can be a sequence gap between the cell-free DNA polynucleotide and the single-stranded adaptor hybridized to the capture probe. This sequence gap can be filled in with a polymerase prior to or concurrent with ligation, which can be effected by a ligase. In some cases, a segment of the cell-free DNA polynucleotide lacking sequence complementarity to the capture probe can form a flap. The flap can be cleaved with an endonuclease prior to or concurrent with ligation, which can be effected by a ligase. The capture probe can be removed prior to or concurrent with circularization of the linear ligation product to yield a circular target polynucleotide. As shown in FIG. 6B, the circular target polynucleotide can then be subjected to primer extension reactions to generate concatemers and extension products using first and second primers.

The amplification products generated according to the methods described herein can then be used with nucleic acid analysis techniques, including nucleic acid sequencing for sequence variant detection. In an aspect, the present disclosure provides a method for identifying a sequence variant in a nucleic acid sample comprising a plurality of cell-free DNA polynucleotides. In some embodiments, the method comprises: (a) forming a plurality of ligation products, wherein an individual member of the ligation products is formed by ligating a cell-free polynucleotide, for example a cell-free DNA polynucleotide, to a single-stranded adaptor of a polynucleotide complex, wherein the polynucleotide complex comprises a first segment of a capture probe hybridized to a cell-free DNA polynucleotide and a second segment of the capture probe hybridized to a single-stranded adaptor, wherein a single-stranded adaptor comprises a unique barcode sequence; (b) circularizing the plurality of ligation products to yield a plurality of circular target polynucleotides; (c) generating a plurality of concatemers, wherein an individual concatemer of the plurality is formed via extension of a first primer that hybridizes to a target polynucleotide via sequence complementarity; (d) generating a plurality of extension products from the concatemers, wherein an individual extension product of the plurality is formed via extension of a second primer that hybridizes to a concatemer via sequence complementarity; (e) sequencing a plurality of the extension products to produce sequencing reads; and (f) identifying a sequence difference between sequencing reads and a reference sequence as the sequence variant, when (i) the sequence difference is detected in a sequencing read of an extension product containing at least two occurrences of the sequence difference, and (ii) the sequence difference occurs in at least two different sequencing reads having distinct barcode sequences.

A barcode sequence, as previously described herein, can refer to a known nucleic acid sequence that allows some feature of a polynucleotide with which the barcode is associated to be identified. Barcodes can comprise any suitable length (in nucleotides), have any suitable melting temperature, and comprise any suitable nucleotide sequence. For example, the nucleotide sequence of each member of a set of barcodes can be sufficiently different from that of every other member of the set such that no member can form a stable duplex with the complement of any other member under moderate or stringent hybridization conditions (e.g., minimally cross-hybridizing). The nucleotide sequence of each member of a minimally cross-hybridizing set can differ from those of every other member by at least two nucleotides. In some embodiments, the barcode sequence of each single-stranded adaptor in a single reaction is different from every other barcode sequence. In some embodiments, the barcode sequence is uniquely associated with a single ligation reaction in a plurality of ligation reactions.

In an aspect, a method for identifying a sequence variant in a nucleic acid sample comprising a plurality of cell-free DNA polynucleotides comprises: (a) forming a plurality of ligation products, wherein an individual member of the ligation products is formed by ligating a cell-free polynucleotide, for example a cell-free DNA polynucleotide, to a single-stranded adaptor of a polynucleotide complex, wherein the polynucleotide complex comprises a first segment of a capture probe hybridized to a cell-free DNA polynucleotide and a second segment of the capture probe hybridized to a single-stranded adaptor; (b) circularizing the plurality of ligation products to yield a plurality of circular target polynucleotides, wherein an individual circular target polynucleotide comprises (i) a first junction between a 5' end of a cell-free DNA polynucleotide and a 3' end of a single-stranded adaptor and (ii) a second junction between a 3' end of the cell-free DNA polynucleotide and a 5' end of the single-stranded adaptor; (c) generating a plurality of concatemers, wherein an individual concatemer of the plurality is formed via extension of a first primer that hybridizes to a target polynucleotide via sequence complementarity; (d) generating a plurality of extension products from the concatemers, wherein an individual extension product of the plurality is formed via extension of a second primer that hybridizes to a concatemer via sequence complementarity; (e) sequencing a plurality of the extension products to produce sequencing reads; and (f) identifying a sequence difference between sequencing reads and a reference sequence as the sequence variant, when (i) the sequence difference is detected in a sequencing read of an extension product containing at least two occurrences of the sequence difference, and (ii) the sequence difference occurs in at least two different sequencing reads having distinct first and second junctions (e.g., junction sequences).

In general, joining ends of a polynucleotide to one-another to form a circular polynucleotide (either directly, or with one or more intermediate adaptor oligonucleotides) produces a junction having a junction sequence. Where the 5' end and 3' end of a polynucleotide are joined via an adaptor polynucleotide, the term "junction" can refer to a junction between the polynucleotide and the adaptor (e.g. one of the 5' end junction or the 3' end junction), or to the junction between the 5' end and the 3' end of the polynucleotide as formed by and including the adaptor polynucleotide. Where the 5' end and the 3' end of a polynucleotide are joined without an intervening adaptor (e.g. the 5' end and 3' end of a single-stranded DNA), the term "junction" can refer to the point at which these two ends are joined. A junction may be identified by the sequence of nucleotides comprising the junction (also referred to as the "junction sequence"). In some embodiments, samples comprise polynucleotides having a mixture of ends formed by natural degradation processes (such as cell lysis, cell death, and other processes by which DNA is released from a cell to its surrounding environment in which it may be further degraded, such as in cell-free polynucleotides), fragmentation that is a byproduct of sample processing (such as fixing, staining, and/or storage procedures), and fragmentation by methods that cleave DNA without restriction to specific target sequences (e.g. mechanical fragmentation, such as by sonication; non-sequence specific nuclease treatment, such as DNase I, fragmentase). Where samples comprise polynucleotides having a mixture of ends, the likelihood that two polynucleotides will have the same 5' end or 3' end is low, and the likelihood that two polynucleotides will independently have both the same 5' end and 3' end is extremely low. Accordingly, in some embodiments, junctions may be used to distinguish different polynucleotides, even where the two polynucleotides comprise a portion having the same target sequence or same adaptor sequence. Where polynucleotide ends are joined without an intervening adaptor, a junction sequence may be identified by alignment to a reference sequence. For example, where the order of two component sequences appears to be reversed with respect to the reference sequence, the point at which the reversal appears to occur may be an indication of a junction at that point. Where polynucleotide ends are joined via one or more adaptor sequences, a junction may be identified by proximity to the known adaptor sequence, or by alignment if a sequencing read is of sufficient length to obtain sequence from both the 5' and 3' ends of the circularized polynucleotide. In some embodiments, the formation of a particular junction is a sufficiently rare event such that it is unique among the circularized polynucleotides of a sample.

In some embodiments, the capture probe is degraded or selectively removed, as described elsewhere herein, prior to the circularizing of (b). In some embodiments, degradation or removal occurs after formation of the ligation product. In some embodiments, the capture probe is degraded. In some embodiments, the capture probe is degraded enzymatically, for example, by an endonuclease. A capture probe can, in some cases, be degraded chemically as described further herein. In some embodiments, the capture probe comprises a tag and the capture probe is selectively removed by a binding element that selectively binds the tag. For example, the tag may be biotin and the binding element may comprise avidin or modified avidin. Further suitable tags and binding elements are described elsewhere herein. In some embodiments, the capture probe comprises a tag and polynucleotide complexes are isolated by binding the tag to a selective binding element which is immobilized to a support. Isolating the polynucleotide complexes can occur prior to degrading or removing the capture probe.

Circularized polynucleotides (or amplification products thereof, e.g., concatemers and extension products, which may have optionally been enriched) can be subjected to a sequencing reaction to generate sequencing reads. A variety of sequencing methodologies are available, particularly high-throughput sequencing methodologies. Examples include, without limitation, sequencing systems manufactured by Illumina (sequencing systems such as HiSeq® and MiSeq®), Life Technologies (Ion Torrent®, SOLID®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300, or more nucleotides in length. In some embodiments, sequencing comprises a sequencing by synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the a and B phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In related sequencing processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. For example, immobilization of the complex can be via a linkage between the polymerase or the primer and the substrate surface. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex, allowing identification of the incorporated nucleotide. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes. For example, the Illumina Genome Analyzer System is based on technology described in WO 98/44151, wherein DNA molecules are bound to a sequencing platform (flow cell) via an anchor probe binding site (otherwise referred to as a flow cell binding site) and amplified in situ on a glass slide. A solid surface on which DNA molecules are amplified typically comprise a plurality of first and second bound oligonucleotides, the first complementary to a sequence near or at one end of a target polynucleotide and the second complementary to a sequence near or at the other end of a target polynucleotide. This arrangement permits bridge amplification, such as described in US20140121116. The DNA molecules are then annealed to a sequencing primer and sequenced in parallel base-by-base using a reversible terminator approach. Hybridization of a sequencing primer may be preceded by cleavage of one strand of a double-stranded bridge polynucleotide at a cleavage site in one of the bound oligonucleotides anchoring the bridge, thus leaving one single strand not bound to the solid substrate that may be removed by denaturing, and the other strand bound and available for hybridization to a sequencing primer.

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a β, γ, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,917,726, 7,033,764, 7,052,847, 7,056,676, 7,170,050, 7,361,466, and 7,416,844; and 20,070,134128).

In some embodiments, the nucleic acids in the sample can be sequenced by ligation. This method typically uses a DNA ligase enzyme to identify the target sequence, for example, as used in the polony method and in the SOLID technology (Applied Biosystems, now Invitrogen). In general, a pool of all possible oligonucleotides of a fixed length is provided, labeled according to the sequenced position. Oligonucleotides are annealed and ligated; the preferential ligation by DNA ligase for matching sequences results in a signal corresponding to the complementary sequence at that position.

Sequencing reads produced by sequencing amplification products generated by the methods herein using various suitable sequencing technologies can then be used for sequence variant detection. In some embodiments, identifying a genuine sequence variant (also referred to as "calling" or "making a call") comprises optimally aligning one or more sequencing reads with a reference sequence to identify differences between the two. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as from a reference genome or from a consensus generated from sequencing reads under analysis. In some embodiments, a reference sequence comprises or consists of sequences of polynucleotides of one or more organisms, such as sequences from one or more bacteria, archaea, viruses, protists, fungi, mammal or other organism. In some embodiments, the reference sequence consists of only a portion of a reference genome, such as regions corresponding to one or more target sequences under analysis (e.g. one or more genes, or portions thereof). For example, for detection of a pathogen (such as in the case of contamination detection), the reference genome is the entire genome of the pathogen (e.g. HIV, HPV, or a harmful bacterial strain, e.g. *E. coli*), or a portion thereof useful in identification, such as of a particular strain or serotype. For further example, for detection of a sequence variant associated with a disease or diseased state, including but not limited to cancer, the reference genome is the entire genome of the subject (e.g. mammal, e.g., human), or a portion thereof useful in identifying a mutated gene. In some embodiments, sequencing reads are aligned to multiple different reference sequences.

In a typical alignment, a base in a sequencing read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affect the resulting alignment. Examples of algorithms for performing alignments include, without limitation, the Smith-Waterman (SW) algorithm, the Needleman-Wunsch (NW) algorithm, algorithms based on the Burrows-Wheeler Transform (BWT), and hash function aligners such as Novoalign (Novocraft Technologies), ELAND (Illumina, San Diego, Calif.), SOAP, and Maq (available at maq.sourceforge.net). One exemplary alignment program, which implements a BWT approach, is Burrows-Wheeler Aligner (BWA) available from the SourceForge web site maintained by Geeknet (Fairfax, Va.). BWT typically occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures. BWA includes two different algorithms, both based on BWT. Alignment by BWA can proceed using the algorithm bwa-short, designed for short queries up to about 200 by with low error rate (<3%) (Li H. and Durbin R. Bioinformatics, 25:1754-60 (2009)). The second algorithm, BWA-SW, is designed for long reads with more errors (Li H. and Durbin R. (2010). Fast and accurate long-read alignment with Burrows-Wheeler Transform. Bioinformatics, Epub.). The bwa-sw aligner is sometimes referred to as "bwa-long", "bwa long algorithm", or similar. An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system. Other non-limiting examples of alignment programs include: BLAT from Kent Informatics (Santa Cruz, Calif.) (Kent, W. J., Genome Research 4: 656-664 (2002)); SOAP2, from Beijing Genomics Institute (Beijing, Conn.) or BGI Americas Corporation (Cambridge, Mass.); Bowtie (Langmead, et al., Genome Biology, 10:R25 (2009)); Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31(2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

According to some embodiments, a sequence difference between sequencing reads and a reference sequence is called as a genuine sequence variant (e.g. existing in the sample prior to amplification or sequencing, and not a result of either of these processes) when it is detected in a sequencing read of an extension product containing at least two occurrences of the sequence difference and occurs in at least two different sequencing reads having distinct barcode sequences (e.g. two different circular polynucleotides, which can be distinguished as a result of having different or distinct barcode sequences). In some embodiments, a sequence difference between sequencing reads an a reference sequence is called as a genuine sequence variant when the sequence difference is detected in a sequencing read of an extension product containing at least two occurrences of the sequence difference and the sequence difference occurs in at least two different sequencing reads having distinct first and second junctions (e.g., junction sequences). Because sequence variants that are the result of amplification or sequencing errors are unlikely to be duplicated exactly (e.g. position and type) on two different polynucleotides comprising the same target sequence, adding these validation parameters can reduce the background of erroneous sequence variants, with a concurrent increase in the sensitivity and accuracy of detecting actual sequence variation in a sample. In some embodiments, a sequence variant having a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate call. In some embodiments, the sequence variant occurs with a frequency of about or less than about 0.1%. In some embodiments, the frequency of a sequence variant is sufficiently above background when such frequency is statistically significantly above the background error rate (e.g. with a p-value of about or less than about 0.05, 0.01, 0.001, 0.0001, or lower). In some embodiments, the frequency of a sequence variant is sufficiently above background when such frequency is about or at least about 2-fold, 3-fold, 4-fold, 5-fold, 6-fold, 7-fold, 8-fold, 9-fold, 10-fold, 25-fold, 50-fold, 100-fold, or more above the background error rate (e.g. at least 5-fold higher). In some embodiments, the background error rate in accurately determining the sequence at a given position is about or less than about 1%, 0.5%, 0.1%, 0.05%, 0.01%, 0.005%, 0.001%, 0.0005%, or lower. In some embodiments, the error rate is lower than 0.001%.

In some embodiments, sequences are analyzed to identify repeat unit length (e.g. the monomer length), the junction formed by circularization, and any true variation with respect to a reference sequence, typically through sequence alignment. Identifying the repeat unit length can include computing the regions of the repeated units, finding the reference loci of the sequences (e.g. when one or more sequences are particularly targeted for amplification, enrichment, and/or sequencing), the boundaries of each repeated region, and/or the number of repeats within each sequencing run. Sequence analysis can include analyzing sequence data for both strands of a duplex. As noted above, in some embodiments, an identical variant that appears the sequences of reads from different polynucleotides from the sample (e.g. circularized polynucleotides having different junctions) is considered a confirmed variant. In some embodiments, a sequence variant may also be considered a confirmed, or genuine, variant if it occurs in more than one repeated unit of the same polynucleotide, as the same sequence variation is likewise unlikely to occur at the same position in a repeated target sequence within the same concatemer. The quality score of a sequence may be considered in identifying variants and confirmed variants, for example, the sequence and bases with quality scores lower than a threshold may be filtered out. Other bioinformatics methods can be used to further increase the sensitivity and specificity of the variant calls.

In some embodiments, statistical analyses may be applied to determination of variants (mutations) and quantitate the ratio of the variant in total DNA samples. Total measurement of a particular base can be calculated using the sequencing data. For example, from the alignment results calculated in previous steps, one can calculate the number of "effective reads," that is, number of confirmed reads for each locus. The allele frequency of a variant can be normalized by the effective read count for the locus. The overall noise level, that is the average rate of observed variants across all loci, can be computed. The frequency of a variant and the overall noise level, combined with other factors, can be used to determine the confidence interval of the variant call. Statistical models such as Poisson distributions can be used to assess the confidence interval of the variant calls. The allele frequency of variants can also be used as an indicator of the relative quantity of the variant in the total sample.

A sequence variant can refer to any variation in sequence relative to one or more reference sequences. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), single nucleotide variants, deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences).

In some embodiments, methylation patterns of polynucleotides are analyzed. For analysis of methylation patterns, the ligation product can be treated with bisulfite prior to circularization, and in some cases, after removal of the capture probe (e.g., via degradation or selective removal). Treatment of a ligation product with bisulfite (e.g., bisulfite treatment) can result in the deamination of unmethylated cytosine to produce uracil in DNA. Methylated cytosines are protected from this conversion to uracil. In subsequent amplification steps, the uracils are amplified as thymines, whereas methylated cytosine residues get amplified as cytosines. Sequencing and subsequent sequence analysis (e.g., detecting C to T mutations) can be used to determine the locations of unmethylated cytosines and methylated cytosines at single-nucleotide resolution.

In another aspect, the disclosure provides a reaction mixture for performing a method in accordance with methods of the disclosure. A reaction mixture can comprise one or more of the various components as described herein with respect to any of the various aspects and methods of the present disclosure. In some embodiments, the disclosure provides a reaction mixture for forming a ligation product comprising a first single-stranded polynucleotide and a second single-stranded polynucleotide. In some embodiments, the reaction mixture comprises (a) a mixture of the first single-stranded polynucleotide, the second single-stranded polynucleotide, and the capture probe wherein a first segment of the capture probe may specifically hybridize with the first single-stranded polynucleotide via sequence complementarity and a second segment of the capture probe may specifically hybridize with the second single-stranded polynucleotide via sequence complementarity; and (b) a ligase that can effect the ligation of the first single-stranded polynucleotide and the second single-stranded polynucleotide, wherein (i) the capture probe comprises RNA and the first and second single-stranded polynucleotides comprise DNA, (ii) the capture probe comprises deoxyuridine, or (iii) the capture probe comprises a tag that selectively binds to a binding element. Examples of the first single-stranded polynucleotide, second single-stranded polynucleotide, and capture probe are described herein, such as with regard to any of the various aspects of the disclosure.

In some embodiments, the first single-stranded polynucleotide, the second single-stranded polynucleotide and the capture probe in a reaction mixture form a complex of polynucleotides wherein a first segment of the capture probe specifically hybridizes with the first single-stranded polynucleotide via sequence complementarity and a second segment of the capture probe specifically hybridizes with the second single-stranded polynucleotide via sequence complementarity. The formation of a complex of polynucleotides comprising the first single-stranded polynucleotide, the second single-stranded polynucleotide and the capture probe can depend on the length (in nucleotides) of the hybridized portion, the degree of sequence complementarity between the first and second single-stranded polynucleotides and the respective segments of the capture probe to which they are each hybridized, and the temperature at which the mixing is conducted, as previously described herein. In some embodiments, the first single-stranded polynucleotide or the second single-stranded polynucleotide is a cell-free polynucleotide, including but not limited to a cell-free DNA or RNA (cfDNA or cfRNA).

In some embodiments, the first single-stranded polynucleotide and the second single-stranded polynucleotide are adjacent to each other when hybridized to the capture probe as described above. A ligase, non-limiting examples of which are provided herein, can effect the ligation of the first single-stranded polynucleotide and the second single-stranded polynucleotide to form a ligation product. In some embodiments, there is a sequence gap between the first single-stranded polynucleotide and the second single-stranded polynucleotide when hybridized to the capture probe as previously described herein. In some embodiments, a reaction mixture comprises a polymerase, non-limiting examples of which are provided herein, that can extend the first single-stranded polynucleotide to fill in a sequence gap between the first single-stranded polynucleotide and the second single-stranded polynucleotide using the capture probe as a template. After a polymerase fills in a sequence gap by extending the first sing-stranded polynucleotide or during this extension reaction, a ligase provided in the reaction mixture can effect the ligation of the first single-stranded polynucleotide and the second-single stranded polynucleotide to form a ligation product. In some embodiments, the second single-stranded polynucleotide comprises at a 5' end a segment lacking sequence complementarity to the capture probe. This segment may not hybridize to the capture probe and can form a segment referred to as a "flap". In some embodiments, a reaction mixture comprises an endonuclease, non-limiting examples of which are provided herein, that can cleave the flap. In some embodiments, a flap endonuclease is provided. Following cleavage of the flap, a ligase provided in a reaction mixture can effect the ligation of the first single-stranded polynucleotide and the second single-stranded polynucleotide to form a ligation product.

Where desired, a capture probe can be removed by degradation or selective removal as described above. Removing a capture probe may occur concurrent with or following the formation of a ligation product. In some embodiments, a first single-stranded polynucleotide and a second single-stranded polynucleotide comprise DNA while the capture probe comprises RNA. In some embodiments, a reaction mixture comprises an RNA endonuclease that can selectively degrade the capture probe comprising RNA. In some embodiments, a first single stranded polynucleotide and a second single-stranded polynucleotide comprise RNA while the capture probe comprises DNA. In some embodiments, a reaction mixture comprises a DNA endonuclease that can selectively degrade the DNA capture probe. In some embodiments, a capture probe comprises one or more deoxyuridines. In some embodiments, a reaction mixture comprises a uracil DNA-glycosylase that can degrade a capture probe comprising one or more deoxyuridines. In some embodiments, a capture probe comprises a tag that selectively binds to a binding element. The capture probe can be removed by a binding element that selectively binds to the tag. In some embodiments, the tag is biotin. Where selectively removing a capture probe comprising a biotin tag is desired, a binding element comprising avidin, modified avidin, or streptavidin can be used.

The first single-stranded polynucleotide can comprise, from a 5' end to a 3' end, a first segment, a second segment, and a third segment wherein the first and second segments do not specifically hybridize to the capture probe via sequence complementarity and the third segment specifically hybridizes to the capture probe via sequence complementarity as described elsewhere herein. In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality. The first segment of the first single-stranded polynucleotide comprising a sequence common to a plurality of different first single-stranded polynucleotides can be useful in downstream processing of ligation products, including but not limited to amplification reactions and sequencing reactions for sequence analysis as described for various other embodiments of the aspects described herein. In some embodiments, the barcode sequence of each first single-stranded polynucleotide in a single reaction is different from every other barcode sequence. In some embodiments, the barcode sequence is uniquely associated with a single ligation reaction in a plurality of ligation reactions.

In some embodiments, a reaction mixture comprises a blocking polynucleotide that hybridizes to a sequence variant via sequence complementarity, wherein the sequence variant is at least 90% identical and less than 100% identical to the second single-stranded polynucleotide. A blocking polynucleotide may be useful for preventing the formation of ligation products comprising the sequence variant, either partially or completely, as described in embodiments of the methods herein.

In some embodiments, a reaction mixture of the present disclosure is contained in a container. Each component may be packaged into different containers or where cross-reactivity and shelf-life permit, combinations of components can be provided in containers. Non-limiting examples of containers include a well, a plate, a tube, a chamber, a flow cell, or a chip.

In another aspect, the disclosure provides kits for performing methods in accordance with the methods of the disclosure. Kits can comprise one or more elements disclosed herein in relation to any of the various aspects, in any combination. In some embodiments, the kit is used for capturing single-stranded target polynucleotides. In some embodiments, a kit comprises a plurality of capture probes, one or more first single-stranded polynucleotides, and instructions for using the plurality of capture probes for capturing one or more single-stranded target polynucleotides. In some embodiments, (a) the capture probe comprises at a 5'end, a segment exhibiting sequence complementarity to a first single-stranded polynucleotide and at a 3'end, a second segment exhibiting sequence complementarity to a single-stranded target polynucleotide; (b) the single-stranded target polynucleotide is a cell-free target polynucleotide; (c) the capture probe comprises at least 10 deoxyuridines; and (d) the one or more first single-stranded polynucleotides comprises from a 5' end to a 3' end a first, a second, and a third segment wherein the first and second segments do not specifically hybridize to the capture probe via sequence complementarity and the third segment specifically hybridizes to the capture probe via sequence complementarity.

In some embodiments, (i) the first segment of each first single-stranded polynucleotide comprises a sequence common to a plurality of different first single-stranded polynucleotides, and (ii) the second segment of each first single-stranded polynucleotide comprises a barcode sequence that is not the same for all first single-stranded polynucleotides in the plurality. Examples of first single-stranded polynucleotides, and various segments thereof are provided herein, such as with regard to any of the various aspects of the disclosure.

In some embodiments, a kit comprises one or more first primers comprising a 3' end sequence that specifically hybridizes to the first or the second segment of the first single-stranded polynucleotide via sequence complementarity. In some embodiments, the one or more first primers comprise, at a 5' end, a first sequencing adaptor lacking sequence complementarity to the first polynucleotide. In some embodiments, a kit comprises one or more second primers comprising a 3' end sequence that specifically hybridize to extension products of the one or more first primers via sequence complementarity. The one or more first and second primers can be used for amplifying the ligation product or a segment of the ligation product in practicing the methods described herein.

In some embodiments, a kit comprises a uracil DNA-glycosylase, an endonuclease, a polymerase, and/or a ligase for practicing the methods of the various embodiments disclosed herein. In some embodiments, a kit comprises one or more capture probes (e.g. DNA probes and/or RNA probes); one or more capture probes labeled with tags (e.g. capture probes labeled with biotin); one or more binding elements that selectively binds a tag (e.g. binding elements comprising avidin or modified avidin or streptavidin); one or more capture probes comprising at least one deoxyuridine; one or more uracil DNA-glycosylases; one or more first single-stranded polynucleotides; one or more second single-stranded polynucleotides; one or more ligases and associated buffers and reagents; one or more polymerases and associated buffers and reagents, including for example dNTPs; one or more endonucleases (e.g. DNA endonuclease and/or RNA endonuclease); one or more blocking polynucleotides; and combinations thereof provided in one or more containers. In some embodiments, a kit comprises a blocking polynucleotide that hybridizes to a sequence variant via sequence complementarity, wherein the sequence variant is at least 90% identical and less than 100% identical to a single-stranded target polynucleotide. A blocking polynucleotide may be useful for preventing the formation of ligation products comprising a sequence variant, either partially or completely, as described in embodiments of the methods herein.

In one aspect, the present disclosure provides a polynucleotide complex that can be used for forming a ligation product. The complex can be any of the complexes formed by a method described herein, such as with regard to any of the various aspects of the disclosure. In some embodiments, a polynucleotide complex comprises a first single-stranded polynucleotide, a second-single stranded polynucleotide, and a capture probe. In some embodiments, the capture probe hybridizes at a 5' end to the first single-stranded polynucleotide and hybridizes at a 3' end to the second single-stranded polynucleotide; the first single-stranded polynucleotide and the second single-stranded polynucleotide are non-contiguous; and the capture probe comprises at least 10 deoxyuridines.

In some embodiments, the first single-stranded polynucleotide of a polynucleotide complex comprises from a 5' end to a 3' end a first, a second, and a third segment. The first segment, second segment, and third segment can comprise sequence elements. In some embodiments, the first and second segments do not specifically hybridize to the capture probe via sequence complementarity and the third segment specifically hybridizes to the capture probe via sequence complementarity. In some embodiments, the first segment does not specifically hybridize to the capture probe via sequence complementarity and the second and third segments specifically hybridize to the capture probe via sequence complementarity. In some embodiments, the first, second, and third segments specifically hybridize to the capture probe via sequence complementarity.

In some embodiments, (i) the first segment of the first single-stranded polynucleotide comprises a sequence common to a plurality of different first single-stranded polynucleotides, and (ii) the second segment of the first single-stranded polynucleotide comprises a barcode sequence that is not the same for all first single-stranded polynucleotides in the plurality.

In some embodiments, one of the first or second single-stranded polynucleotides is a cell-free polynucleotide, including but not limited to a cell-free DNA or RNA (cfDNA or cfRNA). In some embodiments, one of the first or second single-stranded polynucleotides is a fragment of genomic DNA. In some embodiments, one of the first or second single-stranded polynucleotides comprises sequences resulting from a chromosomal rearrangement. In some embodiments, the chromosomal rearrangement is at least one of a deletion, duplication, inversion, and translocation.

Various embodiments of the aspects described herein, including the methods, reaction mixtures, kits, and polynucleotide complexes, comprise a capture probe. A capture probe can be of any suitable length. In some embodiments, a capture probe is at least 30 nucleotides (e.g. at least 50, 60, 70, 80, 90, 100, 150, 200, 250, 300, 350, 400, 450, or 500 nucleotides or more than 500 nucleotides) in length. In some embodiments, a capture probe is more than 100 nucleotides in length. In some embodiments, a capture probe is between 30 and 500 nucleotides (e.g. between 40 and 400 nucleotides, between 50 and 300 nucleotides, or between 75 and 200 nucleotides) in length. A capture probe can comprise nucleotides such as deoxyribonucleotides, ribonucleotides, and combinations thereof. In some embodiments, a capture probe comprises one or more modified nucleotides, such as methylated nucleotides and nucleotide analogs. In some embodiments, a capture probe comprises aminoallyl, biotin, and/or 2' fluoro modifications. In some embodiments, a capture probe comprises modified nucleotides, examples of which include but are not limited to bisphosphates, a series of monophosphates and ARCA, CAP and mCAP. A capture probe may comprise aminoallyl modified nucleotides. Aminoallyl modifications can allow amine reactive moieties, such as a fluorescent dye, biotin, hapten or protein, to be conjugated to the capture probe. Aminoallyl nucleotides can also be used for indirect DNA labeling in PCR, nick translation, primer extensions and cDNA synthesis. In some embodiments, a capture probe comprises 1 modified nucleotide. In some embodiments, a capture probe comprises at least 1 modified nucleotide (e.g. at least 2, 5, 10, 15, 20, 30, 40, 50 modified nucleotides or more than 50 modified nucleotides). In some embodiments, a capture probe comprises at least 1% modified nucleotides (e.g. at least 2%, 3%, 4%, 5%, 6%, 7%, 8%, 9%, 10% modified nucleotides or more than 10% modified nucleotides). In some embodiments, a capture probe comprises between 10% and 100% modified nucleotides (e.g. between 20% and 90% modified nucleotides, between 30% and 80% modified nucleotides, or between 40% and 70% modified nucleotides). In some embodiments, a capture probe comprises deoxyuridines. In some embodiments, a capture probe comprises at least 1 deoxyuridine (e.g. at least 2, 5, 10, 20, 30 deoxyuridines or more than 30 deoxyuridines). In some embodiments, a capture probe comprises at least 1% deoxyuridines (e.g. at least 2%, 3%, 4%, 5%, 6%, 7%, 8%, 9%, 10% deoxyuridines or more than 10% deoxyuridines). In some embodiments, a capture probe comprises between 5% and 50% deoxyuridines.

Certain embodiments of the various aspects of the present disclosure comprise degrading a capture probe. Degrading the capture probe can comprise degrading the capture probe enzymatically. In some embodiments, a capture probe comprising deoxyuridines is degraded by a uracil DNA-glycosylase. In some embodiments, a capture probe is degraded by a nuclease, an endonuclease, an exonuclease, and/or a ribonuclease, including endoribonucleases and exoribonucleases. DNA endonucleases can include type I endonucleases and type II endonucleases. Non-limiting examples of enzymes that can degrade polynucleotides and capture probes include DNase I, micrococcal nuclease, nuclease S1, mung bean nuclease, exonuclease II, exonuclease III, exonuclease IV, exonuclease V, exonuclease VI, exonuclease VII, exonuclease VIII, RNase A, RNase I, RNase III, RNase T1, phosphodiesterase I, phosphodiesterase II, and RNase H.

In some embodiments, the capture probe is degraded chemically. Chemical degradation can be effected by chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron(II) complexes).

Certain embodiments of the various aspects of the present disclosure comprise a capture probe comprising a tag. A tag can comprise a molecular structure that, once attached to a capture probe, provides a distinct characteristic that is not inherent to the capture probe lacking the tag, such as selective binding to a binding element. A capture probe comprising a tag can be selectively removed by a binding element that selectively binds the tag. In some embodiments, a capture probe is modified at an end or a terminus of the probe, such as at a 3' end or a 5' end. In some embodiments, a capture probe is modified at any nucleotide along the length of the capture probe. In some embodiments, a capture probe is modified at one nucleotide. In some embodiments, a capture probe is modified at more than one nucleotide. A tag can be used for the selective removal of the capture probe by using a binding element that selectively binds the tag. Prior to selective removal of the capture probe, a tag can also be used to isolate the complex of polynucleotides such that unhybridized and/or unligated polynucleotides can be removed from the sample volume prior to further analysis and amplification steps. A capture probe may comprise a hapten, biotin or other protein tag. In some embodiments, a tag is a chemical or small molecule tag. In some embodiments of the various aspects of the disclosure, a capture probe comprises a biotin tag. A biotin tag can bind a binding element comprising an avidin, modified avidin, or streptavidin protein. An avidin can be tetrameric or dimeric. An avidin protein may be in a deglycosylated form with modified arginines, such as neutravidin, and can exhibit a more neutral isoelectric point relative to native avidin. Other examples of deglycosylated, neutral forms of avidin include Extravidin (Sigma-Aldrich), NeutrAvidin (Thermo Scientific), NeutrAvidin (Invitrogen), and NeutraLite (Belovo). In some embodiments, a capture probe comprises a biotin tag at a 5' end. In some embodiments, a capture probe comprises more than one biotin tag at a 5' end. In some embodiments, a capture probe comprises a biotin tag at a 3' end. In some embodiments, a capture probe comprises more than one biotin tag at a 3' end. In some embodiments, a capture probe comprises a biotin tag at both a 3' end and a 5' end. In some embodiments, a capture probe comprises at least one biotin tag along the length of the capture probe. In some embodiments, the binding partner comprising avidin, modified avidin, or streptavidin is attached to a solid support, such as a particle or bead. In some embodiments, a particle or bead attached to a binding partner comprising avidin, modified avidin, or streptavidin is magnetic. In some embodiments, the magnetic particles and/or beads comprising a binding partner is used to selectively remove a capture probe by binding the tag to the binding partner as shown in FIG. 4 and a magnet is used to remove the beads. In some embodiments, a plurality of particles or beads attached to a binding partner comprising avidin, modified avidin, or streptavidin are packed into a column and column chromatography is used to remove the capture probe. In some embodiments, a capture probe comprises a digoxigenin tag. A capture probe can comprise at least one digoxigenin tag along the length of the capture probe. A digoxigenin tag can bind a binding element comprising an anti-digoxigenin antibody. In some embodiments, a binding element comprising an anti-digoxigenin antibody is attached to a solid support. In some embodiments, a capture probe comprises a dinitrophenol (DNP) tag. A capture probe can comprise at least one dinitrophenol tag along the length of capture probe. A DNP tag can bind a binding element comprising an anti-DNP antibody. In some embodiments, a binding element comprising an anti-DNP antibody is attached to a solid support. In some embodiments, a capture probe comprises a fluorescein tag. A capture probe can comprise at least one fluorescein tag along the length of the capture probe. A fluorescein tag can bind a binding element comprising an anti-fluorescein antibody. In some embodiments, a binding element comprising an anti-fluorescein antibody is attached to a solid support. Non-limiting examples of pairs of binding partners, one of which may be used as a tag and the other of which may be used as the binding element for removing probes comprising the tag, include antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine); biotin/avidin (or biotin/streptavidin); calmodulin binding protein (CBP)/calmodulin; hormone/hormone receptor; lectin/carbohydrate; peptide/cell membrane receptor; protein A/antibody; hapten/antihapten; enzyme/cofactor; and enzyme/substrate.

The coupling of a tag to a capture probe can be performed using a variety of methods. In some embodiments, tags are coupled to a capture probe by direct attachment or by attachment through one or more linkers (e.g. linker molecules) and the formation of a covalent bond. In some embodiments, tags are coupled to a capture probe by an electrostatic interaction that does not involve a covalent bond. In some embodiments, the tags are chemically attached during in-vitro amplification (e.g. by PCR) using labeled primers. Amplification can comprise a number of different molecular replication or amplification approaches, including but not limited to polymerase chain reaction (PCR), asymmetric PCR, multiplex PCR, nested PCR, hot-start PCR, touchdown PCR, RT-PCR, and methylation-specific PCR. Amplification can be isothermal, including, but not limited to, loop-mediated isothermal amplification (LAMP), strand displacement amplification (SDA), heliembodiment-dependent amplification (HDA), and nicking enzyme amplification reaction (NEAR). In some embodiments, the labels are attached to modified nucleotides which are used to assemble the capture probe. Hapten labeled nucleotides, such as digoxigenin labeled nucleotides, and biotin labeled nucleotides can be incorporated into a capture probe with a variety of DNA or RNA polymerases including SP6, T7, AMV, M-MuLV, DNA Polymerase 1, Taq, Pfu, Klenow fragment, and TdT. Biotin labeled nucleotides can be incorporated into a capture probe with a variety of DNA or RNA polymerases including SP6, T7, AMV, M-MuLV, DNA Polymerase 1, Taq, Pfu, Klenow fragment, and TdT.

In some embodiments of the various aspects herein, one of the first single-stranded polynucleotides and second single-stranded polynucleotides comprises a cell-free polynucleotide, including but not limited to a cell-free DNA or RNA (cfDNA or crRNA). Any cell-free polynucleotide can be used by embodiments of the present disclosure. Cell-free polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and cell-free polynucleotides obtained from the subject may not comprise a sequence variant associated with a disease or disorder. In some embodiments, a subject is suspected of having a disease or disorder, and cell-free polynucleotides obtained from the subject may comprise a sequence variant associated with the disease or disorder. In some embodiments, a subject is pregnant, and cell-free polynucleotides obtained from the subject comprise fetal polynucleotides.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are obtained from a subject. In some embodiments, samples are obtained by venipuncture. In some embodiments, samples are obtained by aspiration.

Various methods and commercial kits are available for obtaining cell-free polynucleotides, such as cell-free DNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of any of the various aspects disclosed herein, one of the first single-stranded polynucleotides and second single-stranded polynucleotides comprises genomic DNA. In some embodiments, at least one of the first single-stranded polynucleotide and second single-stranded polynucleotide is derived from genomic DNA. Genomic DNA can be obtained from a cell sample using various methods and commercial kits available, such as a Qiagen DNeasy Tissue Kit. Genomic DNA can be obtained and purified from a sample using any extraction, isolation, and purification method previously described elsewhere herein. Other non-limiting examples of extraction techniques include: (1) organic extraction followed by ethanol precipitation, e.g., using a phenol/chloroform organic reagent (Ausubel et al., Current Protocols in Molecular Biology (1993)), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., Biotechniques. 1991 10(4): 506-513); and (3) salt-induced nucleic acid precipitation methods (Miller et al., Nucleic Acids Res. 1988 16(3): 1215, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, ethidium bromide).

In some embodiments, at least one of the first single-stranded polynucleotide and second single-stranded polynucleotide comprises fragmented cell-free DNA or fragmented genomic DNA. Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

Some embodiments of the present disclosure comprise primer extension and amplification reactions, such as extending a first single-stranded polynucleotide to fill a sequence gap and amplifying a ligation product or a segment of the ligation product with one or more first and second primers. Primer extension reactions can involve changes in temperature (thermocycling) or a constant temperature (isothermal). In some embodiments, primer extension reactions comprise polymerase chain reaction (PCR). PCR typically involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). Examples of polymerase enzymes that can be used for PCR are thermostable polymerases, including but not limited to, *Thermus thermophilus* HB8; mutant *Thermus oshimai*; *Thermus scotoductus*; *Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some embodiments, a hot start polymerase is used. A hot start polymerase is a modified form of a DNA Polymerase that requires thermal activation. Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Mirus Bio; USB Corp.; Yorkshire Bioscience Ltd; and the like.

In some embodiments, primer extension and amplification reactions comprise isothermal reactions. Non-limiting examples of isothermal amplification technologies are ligase chain reaction (LCR) (e.g. U.S. Pat. Nos. 5,494,810 and 5,830,711); transcription mediated amplification (TMA) (e.g. U.S. Pat. Nos. 5,399,491, 5,888,779, 5,705,365, 5,710, 029); nucleic acid sequence-based amplification (NASBA) (e.g. Malek et al., U.S. Pat. No. 5,130,238); signal mediated amplification of RNA technology (SMART) (e.g. Wharam et al., Nucleic Acids Res. 2001, 29, e54); strand displacement amplification (SDA) (e.g. U.S. Pat. No. 5,455,166); thermophilic SDA (Spargo et al., Mol Cell Probes 1996, 10:247-256; European Pat. No. 0684315); rolling circle amplification (RCA) (e.g. Lizardi, "Rolling Circle Replication Reporter Systems," U.S. Pat. No. 5,854,033); loop-mediated isothermal amplification of DNA (LAMP) (e.g. Notomi et al., "Process for Synthesizing Nucleic Acid," U.S. Pat. No. 6,410,278); heliembodiment-dependent amplification (HDA) (e.g. U.S. Pat. Appl. US20040058378); single primer isothermal amplification (SPIA) (e.g. WO2001020035 and U.S. Pat. No. 6,251,639); and circular helicase-dependent amplification (cHDA) (e.g. U.S. patent application U.S. Ser. No. 10/594,095, abandoned).

In some embodiments of any of the various aspects of the disclosure, a primer may comprise one or more portions or segments. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adaptors (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof. In some embodiments, a primer such as a third primer comprises a sequencing adaptor element, which generally refers to oligonucleotides incorporated at the 5' and/or 3' ends of polynucleotides to facilitate one or more steps of a polynucleotide sequencing reaction. In some embodiments, a sequencing adaptor is used to bind a polynucleotide comprising the sequencing adaptor to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adaptors for flow cell attachment may comprise any suitable sequence compatible with next generation sequencing systems, e.g., 454 Sequencing, Ion Torrent Proton or PGM, and Illumina X10. Non-limiting examples of sequencing adaptors for next generation sequencing methods include P5 and P7 adaptors suitable for use with Illumina sequencing systems; TruSeq Universal Adapter; and TruSeq Indexed Adapter. In some embodiments, a sequencing adaptor can be used to enrich, e.g., via amplification, such as polymerase chain reaction (PCR), for polynucleotides comprising the adaptor sequence. Sequencing adaptors can further comprise a barcode sequence and/or a sample index sequence.

In some embodiments of any of the various aspects of the disclosure, a ligase forms a ligation product comprising a first single-stranded polynucleotide and a second single-stranded polynucleotide. Non-limiting examples of enzymes that can be used for ligation reactions are ATP-dependent double-stranded polynucleotide ligases, NAD+dependent DNA or RNA ligases, and single-strand polynucleotide ligases. Non-limiting examples of ligases are *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre®Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions can contain a buffer component, small molecule ligation enhancers, and other reaction components.

In some embodiments of any of the various aspects of the disclosure, an endonuclease cleaves a flap formed from a 5' end of a second single-stranded polynucleotide. An endonuclease that cleaves the segment of the second single-stranded polynucleotide may be referred to as a 5' nuclease or a flap endonuclease. A flap endonuclease may act as both 5'-3' exonucleases and structure specific endonucleases on specialized DNA structures. Examples of flap endonucleases include, but are not limited to the 5' to 3' exonuclease/endonuclease domain of the *E. coli* DNA polymerase, Taq DNA polymerase or other eubacterial DNA polymerase, or the Archeal or eukaryotic flap endonuclease 1 (FEN1), including human FEN1, murine FEN1, yeast FEN1, *P. horikoshii* FEN1, and Pfu FEN1.

In one aspect, the present disclosure provides systems for designing capture probes, first single-stranded polynucleotides, and/or blocking polynucleotides for use in forming ligation products comprising a first single-stranded polynucleotide and a second single-stranded polynucleotide. The capture probes, first single-stranded polynucleotides, and/or blocking polynucleotides may comprise any of the features described herein, in relation to any of the various aspects of the disclosure. In some embodiments, the system comprises (a) a computer configured to receive a customer request to design capture probes, first single-stranded polynucleotides, and/or blocking polynucleotides; (b) computer readable medium comprising codes that, upon execution by one or more processors, design at least one capture probe, at least one first single-stranded polynucleotide, and/or at least one blocking polynucleotide; and (c) a report generator that sends a report to a recipient, wherein the report contains sequences of the at least one capture probe, at least one first single-stranded polynucleotide, and/or at least one blocking polynucleotide.

In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design capture probes, first single-stranded polynucleotides, and/or blocking polynucleotides for forming a ligation product comprising a second single-stranded polynucleotide, the sequence of which may be provided by the customer. The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, the system comprises a report generator that sends a report to a recipient, wherein the report contains sequences of the at least one capture probe, at least one first single-stranded polynucleotide, and/or at least one blocking polynucleotide. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

In one aspect, the disclosure provides a computer-readable medium comprising codes that, upon execution by one or more processors, implements a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

Example 1: Amplifying Target Polynucleotides with a Degradable Capture Probe

A plurality of second single-stranded polynucleotides, for example cell-free DNAs (cfDNAs), are combined with enzymes, a first single-stranded polynucleotide (e.g. a PCR adaptor), and a capture probe comprising deoxyuridines in an amplification reaction mixture. A cfDNA comprising a target sequence forms a complex with the PCR adaptor, and the capture probe. The relationship between the 3' end of the PCR adaptor and the 5' end of the cfDNA may vary, such as with variation in the location of a fragmentation event that formed the cfDNA. The adaptor and the cfDNA can be immediately adjacent to each other when hybridized to the capture probe as show in panel (A) of FIG. 2, and a ligase in the reaction mixture effects the formation of a ligation product. There can be a sequence gap between the adaptor and the cfDNA hybridized to the capture probe. This sequence gap is filled in with a polymerase in the reaction mixture (see e.g. panel (B) of FIG. 2), which is followed by ligation of the extended adaptor and the cfDNA. A segment of the cfDNA may lack sequence complementarity to the capture probe, which forms a flap as (see e.g. panel (C) of FIG. 2). The flap may be adjacent to the adaptor, or separated by a gap. A flap may also comprise a sequence that is complementary to the capture probe, but has been displaced by an extended adaptor. A flap is cleaved with a flap endonuclease present in the reaction mixture. Where cleavage results in a gap, the gap is filled by adaptor extension, as described above. After cleavage (and extension, where desired), the adaptor and cfDNA are joined by the ligase. A reaction mixture may comprise any or all these end arrangements, such as in the case of multiple cfDNAs comprising a sequence complementary to the capture probe but having different 5' ends. Hybridization may also occur in the presence of a blocking polynucleotide to reduce participation of non-target polynucleotides in the ligation reaction (see e.g. FIG. 5). After ligation, the capture probes comprising deoxyuridines are degraded with uracil DNA-glycosylase. The ligation product is amplified by PCR using first and second primers comprising sequencing adaptors (see e.g. FIG. 2). One primer hybridizes to the cfDNA, preferably at a position that is 3' along the cfDNA relative to the segment of the cfDNA that is complementary to the capture probe. The other primer comprises a common sequence present in each of a plurality of PCR adaptors. Extension of the cfDNA-specific primer produces a complement of the common sequence. The primer comprising the common sequence hybridizes to the extension product, and is itself extended. The amplification products are then sequenced.

Example 2: Amplifying Target Polynucleotides with a Tagged Capture Probe

A plurality of second single-stranded polynucleotides, for example cell-free DNAs (cfDNAs), are combined with enzymes, a first single-stranded polynucleotide (e.g. a PCR adaptor), and a capture probe comprising a biotin tag. A cfDNA comprising a target sequence forms a complex with the PCR adaptor, and the capture probe. The relationship between the 3' end of the PCR adaptor and the 5' end of the cfDNA may vary, such as with variation in the location of a fragmentation event that formed the cfDNA. The adaptor and the cfDNA can be immediately adjacent to each other when hybridized to the capture probe as show in panel (A) of FIG. 4, and a ligase in the reaction mixture effects the formation of a ligation product. There can be a sequence gap between the adaptor and the cfDNA hybridized to the capture probe. This sequence gap is filled in with a polymerase in the reaction mixture (see e.g. panel (B) of FIG. 4), which is followed by ligation of the extended adaptor and the cfDNA. A segment of the cfDNA may lack sequence complementarity to the capture probe, which forms a flap as (see e.g. panel (C) of FIG. 2). The flap may be adjacent to the adaptor, or separated by a gap. A flap may also comprise a sequence that is complementary to the capture probe, but has been displaced by an extended adaptor. A flap is cleaved with a flap endonuclease present in the reaction mixture. Where cleavage results in a gap, the gap is filled by adaptor extension, as described above. After cleavage (and extension, where desired), the adaptor and cfDNA are joined by the ligase. A reaction mixture may comprise any or all these end arrangements, such as in the case of multiple cfDNAs comprising a sequence complementary to the capture probe but having different 5' ends. Hybridization may also occur in the presence of a blocking polynucleotide to reduce participation of non-target polynucleotides in the ligation reaction (see e.g. FIG. 4). After ligation, the capture probes are removed from the reaction by capture on steptavidin-coated beads. Removal may be preceded by denaturation, such that the ligation product is not captured by the beads. Alternatively, the bead capture step may include capture of the ligation product, so as to isolate it from the other reagents in the reaction, followed by a denaturation step to release the ligation product for further processing. The ligation product is amplified by PCR using first and second primers comprising sequencing adaptors (see e.g. FIG. 4). One primer hybridizes to the cfDNA, preferably at a position that is 3' along the cfDNA relative to the segment of the cfDNA that is complementary to the capture probe. The other primer comprises a common sequence present in each of a plurality of PCR adaptors. Extension of the cfDNA-specific primer produces a complement of the common sequence. The primer comprising the common sequence hybridizes to the extension product, and is itself extended. The amplification products are then sequenced.

Example 3: Amplification of Ligation Products from Double-Stranded Capture

Double stranded capture probes comprising deoxyuridines (dU) and corresponding double-stranded target polynucleotides were generated by PCR and purified. Double-stranded target polynucleotides were designed to have either a 0 base flap in a polynucleotide complex when the forward strand was hybridized to a corresponding capture probe and 78 base flap in a polynucleotide complex when the reverse strand was hybridized to a corresponding capture probe; a 10 base flap in a polynucleotide complex when the forward strand was hybridized to a corresponding capture probe and a 68 base flap in a polynucleotide complex when the reverse strand was hybridized to its corresponding capture probe; or a 17 base flap in a polynucleotide complex when the forward strand was hybridized to its corresponding capture probe and a 61 base flap in a polynucleotide complex when the reverse strand was hybridized to its corresponding capture probe.

Figure 7:
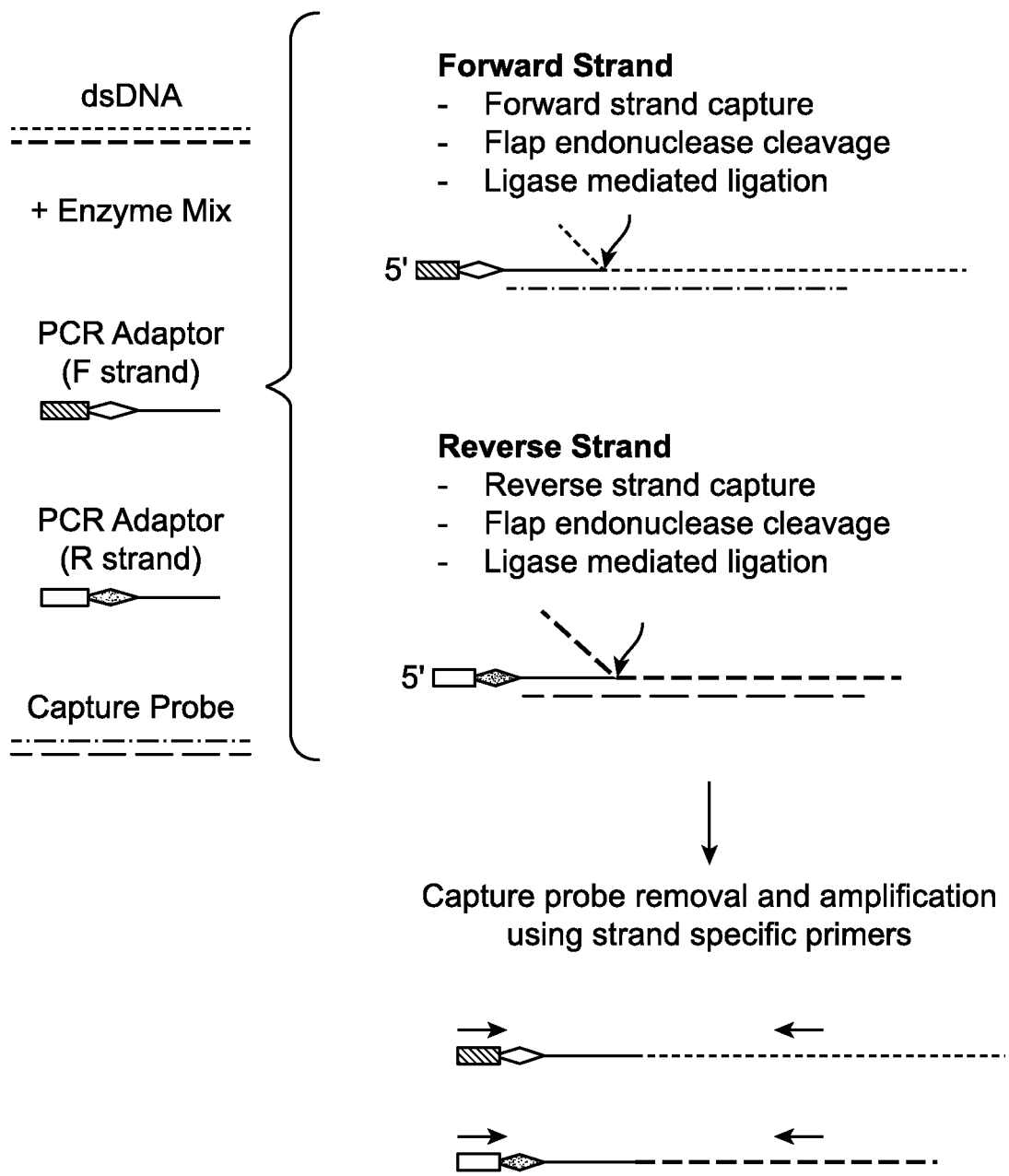
FIG. 7 illustrates polynucleotide capture, flap endonuclease cleavage and ligase mediated ligation of a double-stranded target polynucleotide using a double-stranded capture probe.

To form polynucleotide complexes of both the forward and reverse strands of a target polynucleotide as illustrated in FIG. 7, 10000 molecules of each of capture probes, target polynucleotides and adaptors were mixed and first denatured for 1 minute at 90° C. to generate single-stranded capture probes from double stranded capture probes and single-stranded target polynucleotides from double-stranded target polynucleotides. Polynucleotide complexes were allowed to form by incubating at 60° C. for 4 hours in 30 mM Tris-HCl, pH8.0, 15 mM $MgCl_2$, 0.1% BSA. Ligation products were generated using using Taq ligase plus Afu FEN1 (to cleave the flaps prior to or concurrent with ligation).

Figure 8A:
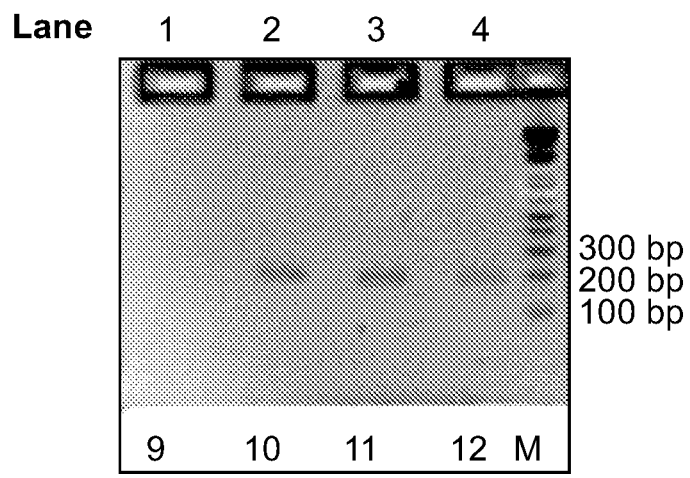
FIGS. 8A and 8B show agarose gels having amplification products generated from ligation products formed using methods of the present disclosure.
Figure 8B:
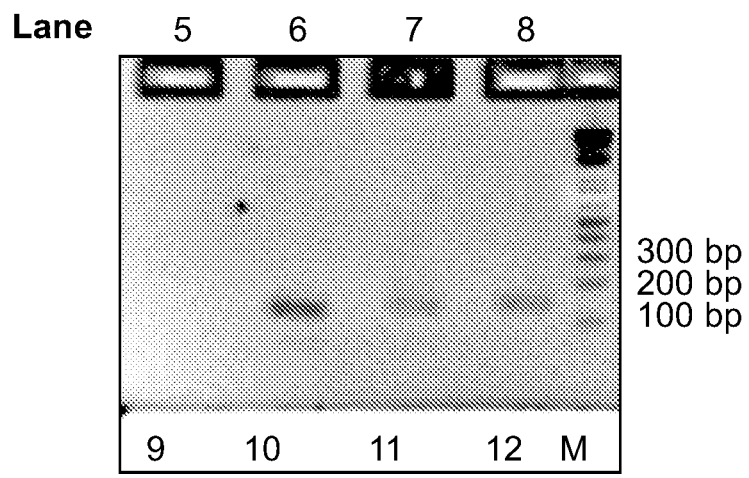

Following ligation, the reactions were treated with USER (uracil specific excision reagent) enzyme to remove the capture probes. Ligation products were then amplified with primers targeting the forward strand ligation product or reverse strand ligation product. The generation of amplification products from ligation products comprising flaps was verified by gel electrophoresis shown in FIGS. 8A and 8B. FIG. 8A shows the amplification product generated from ligation products of forward strand target polynucleotides. FIG. 8B shows the amplification product generated from ligation products of reverse strand target polynucleotides.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of conducting a targeted rolling circle amplification, comprising:
   (a) providing a circular polynucleotide, wherein the circular polynucleotide is formed by: (i) forming a first polynucleotide complex by mixing a plurality of cell-free DNA polynucleotides and a single-stranded adaptor with a capture probe, wherein a first segment of the capture probe hybridizes with a target polynucleotide sequence from the plurality of cell-free DNA polynucleotides via sequence complementarity and a second segment of the capture probe hybridizes with the single-stranded adaptor via sequence complementarity, and 3' end of single-stranded adaptor and 5' end of the target polynucleotide sequence from the plurality of cell-free DNA polynucleotides of the first polynucleotide complex are located adjacent from each other on the capture probe and 5' end of the target polynucleotide sequence from the plurality of cell-free polynucleotides of the first polynucleotide complex lacks a sequence complementarity to the capture probe and forms a flap structure;

(ii) contacting the first polynucleotide complex with a reaction mixture comprising a flap endonuclease under conditions such that the flap structure located on 5' end of the target polynucleotide sequence from the plurality of cell-free polynucleotides of the first polynucleotide complex is cleaved and producing a second polynucleotide complex comprising a cleaved target polynucleotide sequence, the single-stranded adaptor and the capture probe, wherein the flap endonuclease acts as a structure specific endonuclease for cleaving the flap structure located on 5' end of the target polynucleotide sequence of the first polynucleotide complex;

(iii) ligating the cleaved target polynucleotide sequence to the single-stranded adaptor of the second polynucleotide complex, thereby forming a ligation product; and (iv) producing the circular polynucleotide by circularizing the ligation product;

(b) generate a plurality of amplification products comprising concatemers of the ligation product by subjecting an amplification reaction mixture to multiple cycles of a rolling circle amplification, wherein the amplification reaction mixture comprises (i) a polymerase having strand displacement activity, (ii) the circular polynucleotide obtained from step (a), and (iii) at least a first primer that hybridizes to a sequence of at least a segment of the single-stranded adaptor.

2. The method of claim 1, further comprising degrading or selectively removing the capture probe from the second polynucleotide complex prior to step (iv).

3. The method of claim 1, wherein the single stranded adaptor comprises a tag.

4. The method of claim 3, further comprising isolating the first polynucleotide complex or the second polynucleotide complex by immobilizing it directly or indirectly to a support comprising a selective binding agent that specifically binds the tag.

5. The method of claim 1, wherein the method further comprises sequencing the plurality of amplification products to identify a sequence variant of the target polynucleotide sequence comprising at least one of a single nucleotide polymorphism, a single nucleotide variation, an insertion, a deletion, a duplication, an inversion, a translocation, a copy number variation, and a gene fusion.

6. The method of claim 1, further comprising contacting the ligation product with bisulfite to modify unmethylated cytosines in the ligation product to uridines.

7. The method of claim 1, wherein the plurality of amplification products comprising the concatemers of the ligation product is formed via extension of at least the first primer hybridized to the circular polynucleotide in step (b).

8. The method of claim 1, further comprising generating a plurality of extension products, wherein an individual extension product of the plurality of extension products is formed via extension of a second primer that hybridizes to the concatemers of the ligation product of the plurality of amplification products via sequence complementarity.

9. The method of claim 1, wherein at least the first primer also hybridizes to a sequence of at least a segment of the target polynucleotide sequence from the plurality of cell-free DNA polynucleotides.

10. The method of claim 1, wherein at least the first primer comprises a barcode sequence.

* * * * *